United States Patent
Arnon et al.

(10) Patent No.: US 8,620,041 B2
(45) Date of Patent: Dec. 31, 2013

(54) METHOD APPARATUS AND SYSTEM FOR ANALYZING THERMAL IMAGES

(75) Inventors: Israel B. Arnon, Neve Tsuf (IL); Yoel Arieli, Jerusalem (IL)

(73) Assignee: Real Imaging Ltd., Lod (IL)

( * ) Notice: Subject to any disclaimer, the term of this patent is extended or adjusted under 35 U.S.C. 154(b) by 533 days.

(21) Appl. No.: 12/811,099

(22) PCT Filed: Dec. 28, 2008

(86) PCT No.: PCT/IL2008/001685
§ 371 (c)(1),
(2), (4) Date: Jun. 29, 2010

(87) PCT Pub. No.: WO2009/083974
PCT Pub. Date: Jul. 9, 2009

(65) Prior Publication Data
US 2010/0284592 A1    Nov. 11, 2010

Related U.S. Application Data

(60) Provisional application No. 61/006,220, filed on Dec. 31, 2007.

(51) Int. Cl.
*G06K 9/00* (2006.01)
(52) U.S. Cl.
USPC .......................................................... 382/128
(58) Field of Classification Search
USPC .......................................................... 382/128
See application file for complete search history.

(56) References Cited

U.S. PATENT DOCUMENTS

| | | | |
|---|---|---|---|
| 5,946,425 A | 8/1999 | Bove, Jr. et al. |
| 5,961,466 A | 10/1999 | Anbar |
| 6,094,198 A | 7/2000 | Shashua |
| 6,167,151 A | 12/2000 | Albeck et al. |
| 6,201,541 B1 | 3/2001 | Shalom et al. |
| 6,442,419 B1 | 8/2002 | Chu et al. |
| 6,701,081 B1 | 3/2004 | Dwyer et al. |
| 6,765,607 B2 | 7/2004 | Mizusawa et al. |
| 6,801,257 B2 | 10/2004 | Segev et al. |
| 6,850,862 B1 | 2/2005 | Chidichimo et al. |
| 6,965,690 B2 | 11/2005 | Matsumoto |
| 7,072,504 B2 | 7/2006 | Miyano et al. |

(Continued)

FOREIGN PATENT DOCUMENTS

DE    10150918    5/2003
GB    2358752     8/2001

(Continued)

OTHER PUBLICATIONS

International Search Report Dated Jun. 2, 2009 From the International Searching Authority Re.: Application No. PCT/IL2008/001683.
International Search Report Dated Apr. 14, 2009 From the International Searching Authority Re.: Application No. PCT/IL2008/001684.
Written Opinion Dated Jun. 2, 2009 From the International Searching Authority Re.: Application No. PCT/IL2008/001683.
Written Opinion Dated Apr. 14, 2009 From the International Searching Authority Re.: Application No. PCT/IL2008/001684.

(Continued)

*Primary Examiner* — John Pauls
*Assistant Examiner* — Trang Nguyen

(57) ABSTRACT

A method of analyzing a thermal image of a body section is disclosed. The method comprises obtaining a thermospatial representation of the body section, calculating a surface integral of the thermal data over the surface, and determining the likelihood that a thermally distinguishable region is present in the body section, based on a value of the surface integral.

25 Claims, 19 Drawing Sheets

(56) References Cited

U.S. PATENT DOCUMENTS

| | | |
|---|---|---|
| 7,292,719 B2 | 11/2007 | Arnon |
| 2001/0046316 A1 | 11/2001 | Miyano et al. |
| 2004/0151365 A1 | 8/2004 | An Chang et al. |
| 2004/0236225 A1 | 11/2004 | Murphy et al. |
| 2005/0096515 A1* | 5/2005 | Geng .......................... 600/315 |
| 2006/0285731 A1 | 12/2006 | Jiang et al. |
| 2007/0051889 A1 | 3/2007 | Yannacone et al. |
| 2007/0166284 A1* | 7/2007 | Rasmussen et al. ......... 424/93.2 |
| 2007/0213617 A1 | 9/2007 | Berman et al. |
| 2007/0293792 A1 | 12/2007 | Sliwa et al. |

FOREIGN PATENT DOCUMENTS

| | | |
|---|---|---|
| JP | 2007-525244 | 9/2007 |
| WO | WO 2004/098392 | 11/2004 |
| WO | WO 2006/003658 | 1/2006 |
| WO | WO 2009/083973 | 7/2009 |
| WO | WO 2009/083974 | 7/2009 |
| WO | WO 2009/118721 | 10/2009 |

OTHER PUBLICATIONS

Agostini et al. "Evaluation of Feature-Based Registration in Dynamic Infrared Imaging for Breast Cancer Diagnosis", Proceedings of the 28th IEEE EMBS (Engineering in Medicine and Biology) Annual International Conference, New York City, USA, Aug. 30-Sep. 3, 2006, XP031235634, p. 953-956, Aug. 30, 2006. p. 953, § 2, 3.
Bichinho et al. "A Computer Tool for the Fusion and Visualization of Thermal and Magnetic Resonance Images", Journal of Digital Imaging [Online], XP002527797, Retrieved from the Internet: URL:http://www.springerlink.com/content/5w157t2747272m65/>. p. 3, Col. 1, Line 5-Col. 2, Line 6, Fig.1.
Deng et al. "Enhancement of Thermal Diagnostics on Tumors Underneath the Skin by Induced Evaporation", Proceedings of the 2005 27th Annual International Conference of the Engineering in Medicine and Biology Society, Shanghai, China, Sep. 1-4, 2005, IEEE-EMBS 2005, XP002519610, 7: 7525-7528, 2005. Passage Bridging p. 7526 and p. 7527, Abstract, Figs.4, 5.
Kaczmarek et al. "Optical Excitation Methods in Active Dynamic Thermography in Medical Diagnostics", Proceedings of the SPIE—The International Society for Optical Engineering SPIE, XP002519609, 5566(1): 120-126, 2004. p. 121, Last §, p. 123, First §, Fig.3.
Moderhak et al. "Problems of 3D Breast Imaging", Gdansk University of Technology, Department of Biomedical Engineering, 2 P.
Communication Pursuant to Article 94(3) EPC Dated Jan. 12, 2011 From the European Patent Office Re. Application No. 08867385.0.
Response Dated Jul. 12, 2011 to Communication Pursuant to Article 94(3) EPC of Jan. 12, 2011 From the European Patent Office Re. Application No. 08867385.0.
International Search Report Dated May 18, 2009 From International Searching Authority Re.: Application No. PCT/IL2008/001685.
Written Opinion Dated May 18, 2009 From the International Searching Authority Re.: Application No. PCT/IL2008/001685.
International Preliminary Report on Patentability Dated Oct. 7, 2010 From the International Bureau of WIPO Re. Application No. PCT/IL2008/001684.
Communication Pursuant to Article 94(3) EPC Dated Dec. 21, 2010 From the European Patent Office Re. Application No. 08866783.7.
Response Dated Jun. 21, 2011 to Communication Pursuant to Article 94(3) EPC of Dec. 21, 2010 From the European Patent Office Re. Application No. 08866783.7.
International Preliminary Report on Patentability Dated Jul. 15, 2010 From the International Bureau of WIPO Re. Application No. PCT/IL2008/001683.
International Preliminary Report on Patentability Dated Jul. 15, 2010 From the International Bureau of WIPO Re. Application No. PCT/IL2008/001685.
Translation of Office Action Dated Jun. 22, 2011 From the State Intellectual Property Office of the People's Republic of China Re. Application No. 200880127685.9.
Aksenov et al. "3D Thermography for Quantification of Heat Generation Resulting From Inflammation", Proceedings of the 8th 3D Modelling Symposium, Paris, France, XP))2523191, 11 P., 2003.
Deng et al. "Mathematical Modeling of Temperature Mapping Over Skin Surface and Its Implementation in Thermal Disease Diagnostics", Computers in Biology and Medicine, XP002523192, 34(6): 495-521, Sep. 2004. Abstract, p. 497.
Lipari et al. "Advanced Infrared Image Processing for Breast Cancer Risk Assessment", Proceedings of the 19th Annual International Conference of the IEEE/EMBS Engineering in Medicine and Biology Society, Chicago, IL, USA, Oct. 30-Nov. 2, 1997, XP010325780, 2: 673-676, Oct. 30, 1997. Abstract, Sections II, III, Fig.3.
Tan et al. "A Novel Cognitive Interpretation of Breast Cancer Thermography With Complementary Learning Fuzzy Neural Memory Structure", Expert Systems With Applications, XP005919120, 33(3): 652-666, Mar. 13, 2007. Abstract, p. 658-659, Section 4, Fig.5.
Communication Pursuant to Article 94(3) EPC Dated Aug. 16, 2011 From the European Patent Office Re. Application No. 08873559.2.
Communication Pursuant to Article 94(3) EPC Dated Feb. 8, 2012 From the European Patent Office Re. Application No. 08867385.0.
Communication Pursuant to Article 94(3) EPC Dated Oct. 18, 2012 From the European Patent Office Re. Application No. 08873559.2.
Office Action Dated Dec. 2, 2012 From the Israel Patent Office Re. Application No. 206644 and Its Translation Into English.
Official Action Dated Oct. 15, 2012 From the US Patent and Trademark Office Re. U.S. Appl. No. 12/934,647.
Official Action Dated Nov. 19, 2012 From the US Patent and Trademark Office Re. U.S. Appl. No. 12/811,097.
Translation of Notice of Reason for Rejection Dated Dec. 21, 2012 From the Japanese Patent Office Re. Application No. 2010-541136.
Translation of Notice of Reason for Rejection Dated Dec. 21, 2012 From the Japanese Patent Office Re. Application No. 2010-541137.
Translation of Office Action Dated Feb. 22, 2012 From the State Intellectual Property Office of the People's Republic of China Re. Application No. 200880127684.4.
Barone et al. "A Biomedical Application Combining Visible and Thermal 3D Imaging", INGEGRAF (Asociacion Espanola de Ingenieria Grafica) 2006, Retrieved From the Internet, p. 1-9, 2006.
Sato et al. "Image Guidance of Breast Cancer Surgery Using 3-D Ultrasound Images and Augmented Reality Visualization", IEEE Transactions on Medical Imaging, 17(5): 681-693, Oct. 1998.
Wikipedia "Surface Integral", Wikipedia, the Free Encyclopedia, Retrieved From the Internet, 3 P., Jan. 23, 2012.
Communication Pursuant to Article 94(3) EPC Dated Apr. 25, 2013 From the European Patent Office Re. Application No. 08867385.0.
Translation of Office Action Dated Dec. 14, 2012 From the State Intellectual Property Office of the People's Republic of China Re. Application No. 200880127684.4.
Wedemeyer et al. "Numerical Simulation of the Three-Dimensional Structure and Dynamics of the Non-Magnetic Solar Chromosphere", Astronomy & Astrophysics, 414(3): 1121-1137, Feb. 2004.
Official Action Dated Jun. 19, 2013 From the US Patent and Trademark Office Re. U.S. Appl. No. 12/811,097.
Bichinho et al. "A Computer Tool for the Fusion and Visualization of Thermal and Magnetic Resonance Images", Journal of Digital Imaging, 22(5): 527-534, Oct. 2009.
Notice of Allowance Dated Oct. 16, 2013 From the US Patent and Trademark Office Re. U.S. Appl. No. 12/811,097.
Office Action Dated Sep. 8, 2013 From the Israel Patent Office Re. Application No. 206663 and Its Translation Into English.
Translation of Decision on Rejection Dated Aug. 6, 2013 From the State Intellectual Property Office of the People's Republic of China Re. Application No. 200880127684.4.

\* cited by examiner

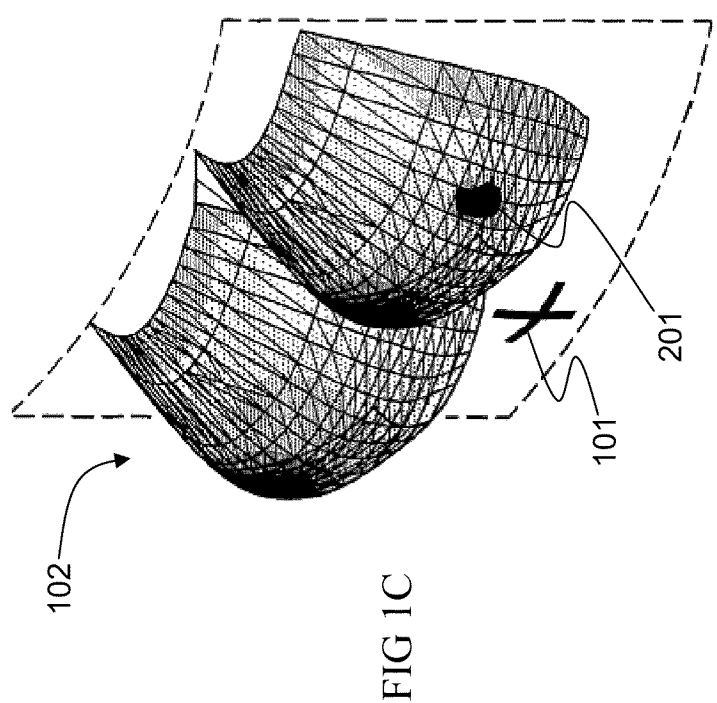

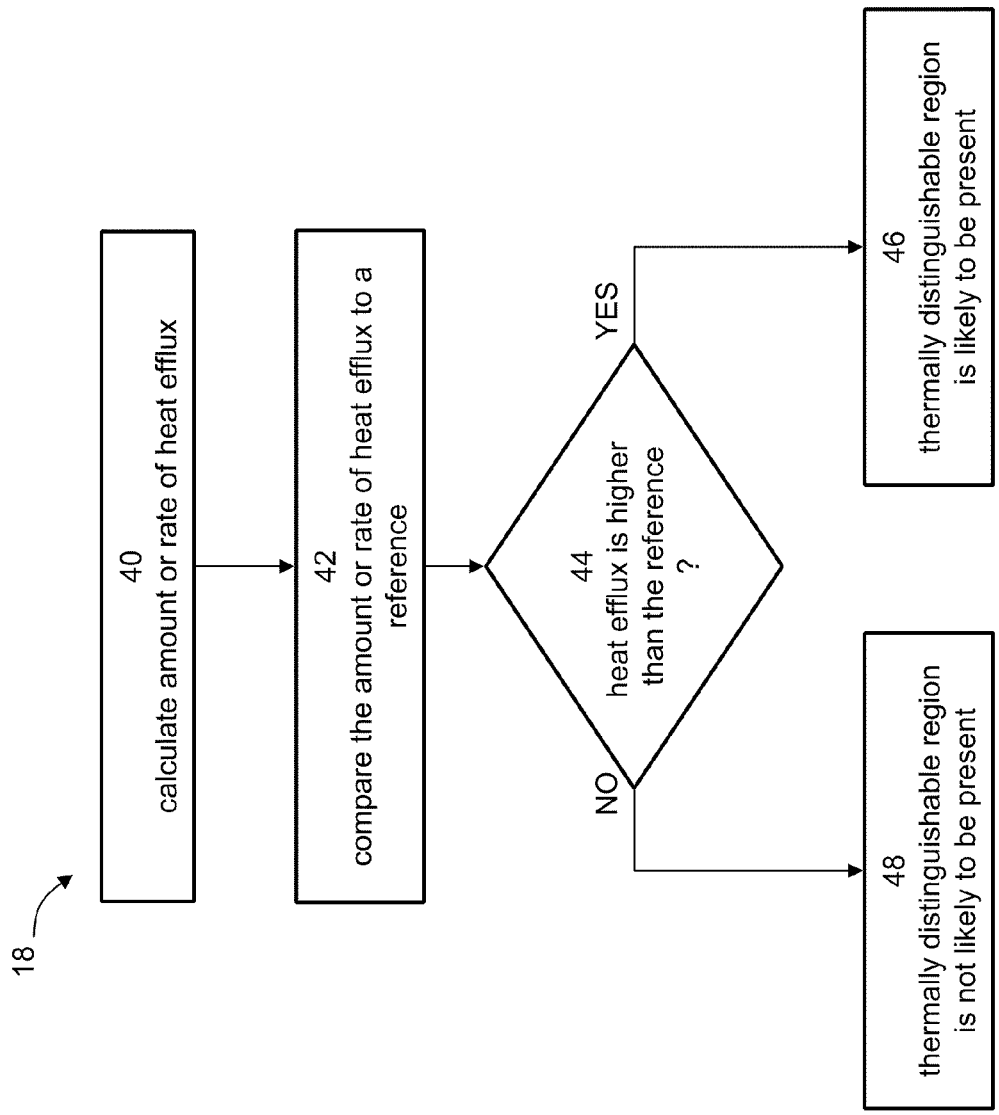

METHOD APPARATUS AND SYSTEM FOR ANALYZING THERMAL IMAGES

RELATED APPLICATIONS

This Application is a National Phase of PCT Patent Application No. PCT/IL2008/001685 having International filing date of Dec. 28, 2008, which claims the benefit of U.S. Provisional Patent Application No. 61/006,220 filed on Dec. 31, 2007. The contents of the above Applications are all incorporated herein by reference.

FIELD AND BACKGROUND OF THE INVENTION

The present invention, in some embodiments thereof, relates to thermal images and, more particularly, but not exclusively, to the analysis of thermal images.

The use of imaging in diagnostic medicine dates back to the early 1900s. Presently there are numerous different imaging modalities at the disposal of a physician allowing imaging of hard and soft tissues and characterization of both normal and pathological tissues.

Infra red imaging is utilized for characterizing a thermally distinguishable site in a human body for the purposes of identifying inflammation. Infrared cameras produce two-dimensional images known as thermographic images. A thermographic image is typically obtained by receiving from the body of the subject radiation at any one of several infrared wavelength ranges and analyzing the radiation to provide a two-dimensional temperature map of the surface. The thermographic image can be in the form of either or both of a visual image and corresponding temperature data. The output from infrared cameras used for infrared thermography typically provides an image comprising a plurality of pixel data points, each pixel providing temperature information which is visually displayed, using a color code or grayscale code. The temperature information can be further processed by computer software to generate for example, mean temperature for the image, or a discrete area of the image, by averaging temperature data associated with all the pixels or a sub-collection thereof.

Based on the thermographic image, a physician diagnoses the site, and determines, for example, whether or not the site includes an inflammation while relying heavily on experience and intuition.

U.S. Pat. No. 7,072,504 discloses an approach which utilizes two infrared cameras (left and right) in combination with two visible light cameras (left and right). The infrared cameras are used to provide a three-dimensional thermographic image and the visible light cameras are used to provide a three-dimensional visible light image. The three-dimensional thermographic and three-dimensional visible light images are displayed to the user in an overlapping manner.

International Patent Publication No. 2006/003658, the contents of which are hereby incorporated by reference, discloses a system which includes non-thermographic image data acquisition functionality and thermographic image data acquisition functionality. The non-thermographic image data acquisition functionality acquires non-thermographic image data, and the thermographic image data acquisition functionality acquires thermographic image data.

U.S. Pat. No. 7,292,719, the contents of which are hereby incorporated by reference discloses a system for determining presence or absence of one or more thermally distinguishable objects in a living body. A combined image generator configured combines non-thermographic three-dimensional data of a three-dimensional tissue region in the living body with thermographic two-dimensional data of the tissue region so as to generate three-dimensional temperature data associated with the three-dimensional tissue region.

Also of interest is U.S. Pat. No. 6,442,419 disclosing a scanning system including an infrared detecting mechanism which performs a 360° data extraction from an object, and a signal decoding mechanism, which receives electrical signal from the infrared detecting mechanism and integrates the signal into data of a three-dimensional profile curved surface and a corresponding temperature distribution of the object.

Additional background art includes U.S. Pat. No. 6,850,862 which discloses the generation of three-dimensional maps of temperature distribution, and U.S. Pat. No. 5,961,466 which discloses detection of breast cancer from a rapid time series of infrared images which is analyzed to detect changes in the distribution of thermoregulatory frequencies over different areas of the skin.

SUMMARY OF THE INVENTION

According to an aspect of some embodiments of the present invention there is provided a method of analyzing a thermal image of a body section. The method comprises, obtaining a thermospatial representation having thermal data representing the thermal image and spatial data representing a non-planar surface of the body section, the thermal data being associated with the spatial data; calculating a surface integral of the thermal data over the surface; and determining the likelihood that a thermally distinguishable region is present in the body section, based on a value of the surface integral.

According to an aspect of some embodiments of the present invention there is provided a method of monitoring evolution of a tumor in a body section. The method comprises: (a) generating a series of thermospatial representations, each having thermal data representing the thermal image and spatial data representing a non-planar surface of the body section, the thermal data being associated with the spatial data; (b) for each thermospatial representation, calculating a surface integral of respective thermal data over respective surface, thereby providing a series of surface integral values; and (c) comparing at least two of the surface integral values, and using the comparison for assessing whether the size of the tumor varies, thereby monitoring the evolution of the tumor.

According to some embodiments of the invention the method further comprises applying a destructive treatment to the tumor, wherein the comparison is used for assessing whether the size of the tumor is stable reduced.

According to some embodiments of the invention the determination of the likelihood comprises comparing the surface integral value to a value of at least one reference surface integral corresponding to a reference thermospatial representation.

According to still further features in the described preferred embodiments the method further comprises using the surface integral value for calculating an amount or rate of heat efflux from the body section.

According to some embodiments of the invention the determination of the likelihood comprises comparing the amount or rate of heat efflux to an amount or rate of heat efflux calculated using a value of at least one reference surface integral corresponding to a reference thermospatial representation.

According to still further features in the described preferred embodiments the method further comprises using the surface integral value for calculating a statistical moment of the thermal data over the surface.

According to some embodiments of the invention the determination of the likelihood comprises comparing the statistical moment to a statistical moment calculated using a value of at least one reference surface integral corresponding to a reference thermospatial representation.

According to still further features in the described preferred embodiments the method further comprises defining a region-of-interest within the surface wherein the surface integral is calculated over the region-of-interest.

According to still further features in the described preferred embodiments the method further comprises slicing the surface to a plurality of slices wherein the surface integral is calculated separately for each slice.

According to still further features in the described preferred embodiments the method further comprises iteratively repeating the slicing and the calculation of the surface integral.

According to some embodiments of the invention the determination of the likelihood comprises calculating variation of a value of the surface integral among different slices.

According to some embodiments of the invention the determination of the likelihood comprises comparing the variations to variations of at least one reference surface integral over a reference thermospatial representation.

According to some embodiments of the invention the reference thermo spatial representation(s) describes a reference body other than the body section and being similar in shape thereto.

According to some embodiments of the invention the reference thermo spatial representation(s) comprises history data of the body section.

According to some embodiments of the invention the reference surface integral corresponds to a reference body section other than the body section and being devoid of thermally distinguishable region therein.

According to some embodiments of the invention the body section is a first breast of a woman and the reference body section is a second breast of the woman.

According to some embodiments of the invention the body section is a part of a first breast of a woman and the reference body section is a part of a second breast of the woman.

According to some embodiments of the invention the spatial data comprises data representing a surface of tissue being nearby to the body section and the method comprises defining a spatial boundary between the surface of the body section and the surface of the nearby tissue.

According to an aspect of some embodiments of the present invention there is provided apparatus for analyzing a thermal image of a body section. The apparatus comprises an input unit for receiving a thermospatial representation having thermal data representing the thermal image and spatial data representing a non-planar surface of the body section, the thermal data being associated with the spatial data; an integration unit for calculating a surface integral of the thermal data over the surface; and an output unit for issuing a report regarding a value of the surface integral.

According to an aspect of some embodiments of the present invention there is provided an imaging and processing system. The imaging and processing system comprises a thermospatial imaging system operable to provide a thermospatial representation of a body section, and the apparatus described herein.

According to some embodiments of the invention the apparatus further comprises a heat calculator for calculating an amount or rate of heat efflux from the body section using a value of the surface integral.

According to some embodiments of the invention the apparatus further comprises a statistical moment calculator for calculating statistical moment of the thermal data over the surface using a value of the surface integral.

According to some embodiments of the invention the apparatus further comprises a slicing unit for slicing the surface to a plurality of slices wherein the surface integral is calculated separately for each slice.

According to some embodiments of the invention the spatial data comprises data representing a surface of tissue being nearby to the body section and the apparatus comprises a boundary definition unit for defining a spatial boundary between the surface of the body section and the surface of the nearby tissue.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 1A-C are schematic illustrations of a thermospatial representation, according to some embodiments of the present invention;

FIGS. 3A-C are fragmentary flow chart diagram illustrating some embodiments in which the method determines the likelihood that a thermally distinguishable region is present in body section;

DESCRIPTION OF SPECIFIC EMBODIMENTS OF THE INVENTION

Figure 1B:
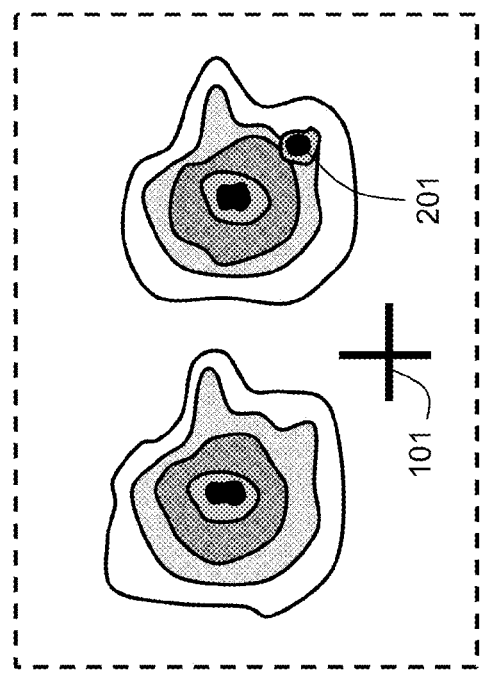

The present invention, in some embodiments thereof, relates to thermal images and, more particularly, but not exclusively, to the analysis of thermal images.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

The present inventors have devised an approach which enables the analysis of a thermal image, e.g., for the purpose of determining the likelihood that the image indicates presence of a thermally distinguishable region. When the thermal image is of a body section such as a breast of a woman, the analysis of the present embodiments can be used to extract properties of the underlying tissue. For example, determination of the likelihood that a thermally distinguished region is present in the body section can be used to for assessing whether or not the body section has a pathology such as a tumor.

The analysis according to some embodiments of the present invention is based on surface information obtained from the surface of the body section. Generally, the surface information is used for calculating a surface integral as further detailed hereinunder. In some embodiments of the present invention the surface integral relates to the likelihood that a thermally distinguishable region, e.g., a tumor or an inflammation, is present in the body section.

An elevated temperature is generally associated with a tumor due to the metabolic abnormality of the tumor and proliferation of blood vessels (angiogenesis) at and/or near the tumor. In a cancerous tumor the cells double faster and thus are more active and generate more heat. This tends to enhance the temperature differential between the tumor itself and the surrounding temperature. The present embodiments can therefore be used for diagnosis of cancer, particularly, but not exclusively breast cancer.

The determination of the likelihood that a thermally distinguishable region is present in the body section is based on the value of the surface integral and can be done in more than one way. For example, the value of the surface integral can be compared to a value of one or more reference surface integrals, or it can be used for further calculations such as calculations of the amount or rate of heat efflux from the body section, calculations of various moments such as standard deviations, and the like. Representative examples of various calculations using the surface integral are provided hereinunder.

The surface information used for the analysis comprises spatial information as well as thermal information.

The spatial information comprises data pertaining to geometric properties of a non-planar surface which at least partially encloses a three-dimensional volume. Generally, the non-planar surface is a two-dimensional object embedded in a three-dimensional space. Formally, a non-planar surface is a metric space induced by a smooth connected and compact Riemannian 2-manifold. Ideally, the geometric properties of the non-planar surface would be provided explicitly for example, the slope and curvature (or even other spatial derivatives or combinations thereof) for every point of the non-planar surface. Yet, such information is rarely attainable and the spatial information is provided for a sampled version of the non-planar surface, which is a set of points on the Riemannian 2-manifold and which is sufficient for describing the topology of the 2-manifold. Typically, the spatial information of the non-planar surface is a reduced version of a 3D spatial representation, which may be either a point-cloud or a 3D reconstruction (e.g., a polygonal mesh or a curvilinear mesh) based on the point cloud. The 3D spatial representation is expressed via a 3D coordinate system, such as, but not limited to, Cartesian, Spherical, Ellipsoidal, 3D Parabolic or Paraboloidal coordinate 3D system.

The term "surface" is used herein as an abbreviation of the term "non-planar surface".

The spatial data, in some embodiments of the present invention, can be in a form of an image. Since the spatial data represent the surface such image is typically a two-dimensional image which, in addition to indicating the lateral extent of body members, further indicates the relative or absolute distance of the body members, or portions thereof, from some reference point, such as the location of the imaging device. Thus, the image typically includes information residing on a non-planar surface of a three-dimensional body and not necessarily in the bulk. Yet, it is commonly acceptable to refer to such image as "a three-dimensional image" because the non-planar surface is conveniently defined over a three-dimensional system of coordinate. Thus, throughout this specification and in the claims section that follows, the terms "three-dimensional image" and "three-dimensional representation" primarily relate to surface entities.

The thermal information comprises data pertaining to heat evacuated from or absorbed by the surface. Since different parts of the surface generally evacuate or absorb different amount of heat, the thermal information comprises a set of tuples, each comprising the coordinates of a region or a point on the surface and a thermal numerical value (e.g., temperature, thermal energy) associated with the point or region. The thermal information can be transformed to visible signals, in which case the thermal information is in the form of a thermographic image. The terms "thermographic image" and thermal information are used interchangeably throughout the specification without limiting the scope of the present invention in any way. Specifically, unless otherwise defined, the use of the term "thermographic image" is not to be considered as limited to the transformation of the thermal information into visible signals. For example, a thermographic image can be stored in the memory of a computer readable medium as a set of tuples as described above.

The surface information (thermal and spatial) of a body is typically in the form of a synthesized representation which includes both thermal data representing the thermal image and spatial data representing the surface, where the thermal data is associated with the spatial data (i.e., a tuple of the spatial data is associated with a heat-related value of the thermal data). Such representation is referred to as a thermospatial representation. The thermospatial representation can be in the form of digital data (e.g., a list of tuples associated with digital data describing thermal quantities) or in the form of an image (e.g., a three-dimensional image color-coded or grey-level coded according to the thermal data). A thermospatial representation in the form of an image is referred to hereinafter as a thermospatial image.

The thermospatial image is defined over a 3D spatial representation of the body and has thermal data associated with a surface of the 3D spatial representation, and arranged gridwise over the surface in a plurality of picture-elements (e.g., pixels, arrangements of pixels) each represented by an intensity value or a grey-level over the grid. It is appreciated that the number of different intensity value can be different from the number of grey-levels. For example, an 8-bit display can generate 256 different grey-levels. However, in principle, the number of different intensity values corresponding to thermal information can be much larger. As a representative example, suppose that the thermal information spans over a range of 37° C. and is digitized with a resolution of 0.1° C. In this case, there are 370 different intensity values and the use of grey-levels is less accurate by a factor of approximately 1.4. In some embodiments of the present invention the processing of thermal data is performed using intensity values, and in some embodiments of the present invention the processing of thermal data is performed using grey-levels. Combinations of the two (such as double processing is also contemplated).

The term "pixel" is sometimes abbreviated herein to indicate a picture-element. However, this is not intended to limit the meaning of the term "picture-element" which refers to a unit of the composition of an image.

When the thermospatial representation is in the form of digital data, the digital data describing thermal properties can also be expressed either in terms of intensities or in terms of grey-levels as described above. Digital thermospatial representation can also correspond to thermospatial image whereby each tuple corresponds to a picture-element of the image.

Typically, one or more thermographic images are mapped onto the surface of the 3D spatial representation to form the thermospatial representation. The thermographic image to be mapped onto the surface of the 3D spatial representation preferably comprises thermal data which are expressed over the same coordinate system as the 3D spatial representation. Any type of thermal data can be used. In one embodiment the thermal data comprises absolute temperature values, in another embodiment the thermal data comprises relative temperature values each corresponding, e.g., to a temperature difference between a respective point of the surface and some reference point, in an additional embodiment, the thermal data comprises local temperature differences. Also contemplated, are combinations of the above types of temperature data, for example, the thermal data can comprise both absolute and relative temperature values, and the like.

Typically, but not obligatorily, the information in the thermographic image also includes the thermal conditions (e.g., temperature) at one or more reference markers.

The mapping of the thermographic image onto the surface of the 3D spatial representation is by positioning the reference markers, for example (e.g., by comparing their coordinates in the thermographic image with their coordinates in the 3D spatial representation), to thereby match also other points hence to form the synthesized thermospatial representation.

Optionally and preferably, the mapping of thermographic images is accompanied by a correction procedure in which thermal emissivity considerations are employed.

The thermal emissivity of a body member is a dimensionless quantity defined as the ratio between the amount of thermal radiation emitted from the surface of the body member and the amount of thermal radiation emitted from a black body having the same temperature as the body member. Thus, the thermal emissivity of an idealized black body is 1 and the thermal emissivity of all other bodies is between 0 and 1. It is commonly assumed that the thermal emissivity of a body is generally equal to its thermal absorption factor.

The correction procedure can be performed using estimated thermal characteristics of the body of interest. Specifically, the thermographic image is mapped onto a non-planar surface describing the body taking into account differences in the emissivity of regions on the surface of the body. A region with a different emissivity value compared to its surrounding, can be, for example, a scarred region, a pigmented region, a nipple region on the breast, a nevus. Additionally, the emissivity values of subjects with different skin colors may differ.

In some embodiments of the present invention, the thermographic image is weighted according to the different emissivity values of the surface. For example, when information acquired by a thermal imaging device include temperature or energy values, at least a portion of the temperature or energy values can be divided by the emissivity values of the respective regions on the surface of the body. One of ordinary skill in the art will appreciate that such procedure results in effective temperature or energy values which are higher than the values acquired by the thermal imaging device. Since different regions may be characterized by different emissivity values, the weighted thermographic image provides better estimate regarding the heat emitted from the surface of the body.

Figure 1A:
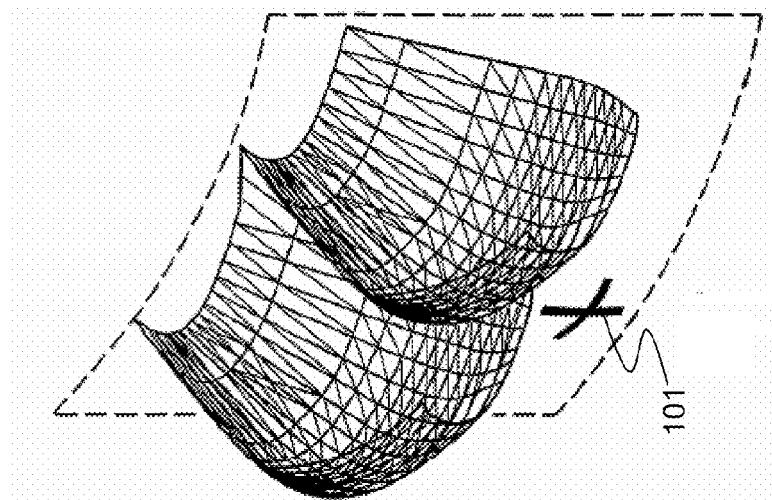

A representative example of a synthesized thermospatial image for the case that the body comprise the breasts of a woman is illustrated in FIGS. 1a-c, showing a 3D spatial representation illustrated as a non-planar surface (FIG. 1a), a thermographic image illustrated as planar isothermal contours (FIG. 1b), and a synthesized thermospatial image formed by mapping the thermographic image on a surface of the 3D spatial representation (FIG. 1c). As illustrated, the thermal data of the thermospatial image is represented as grey-level values over a grid generally shown at 102. It is to be understood that the representation according to grey-level values is for illustrative purposes and is not to be considered as limiting. As explained above, the processing of thermal data can also be performed using intensity values. Also shown in FIGS. 1a-c, is a reference marker 101 which optionally, but not obligatorily, can be used for the mapping.

The 3D spatial representation, thermographic image and synthesized thermospatial image can be obtained in any technique known in the art, such as the technique disclosed in International Patent Publication No. WO 2006/003658, U.S. Published Application No. 20010046316, and U.S. Pat. Nos. 6,442,419, 6,765,607, 6,965,690, 6,701,081, 6,801,257, 6,201,541, 6,167,151, 6,167,151, 6,094,198 and 7,292,719.

Some embodiments of the invention can be embodied on a tangible medium such as a computer for performing the method steps. Some embodiments of the invention can be embodied on a computer readable medium, comprising computer readable instructions for carrying out the method steps. Some embodiments of the invention can also be embodied in electronic device having digital computer capabilities arranged to run the computer program on the tangible medium or execute the instruction on a computer readable medium. Computer programs implementing method steps of the present embodiments can commonly be distributed to users on a tangible distribution medium. From the distribution medium, the computer programs can be copied to a hard disk or a similar intermediate storage medium. The computer programs can be run by loading the computer instructions either from their distribution medium or their intermediate storage medium into the execution memory of the computer, configuring the computer to act in accordance with the method of this invention. All these operations are well-known to those skilled in the art of computer systems.

Figure 2:
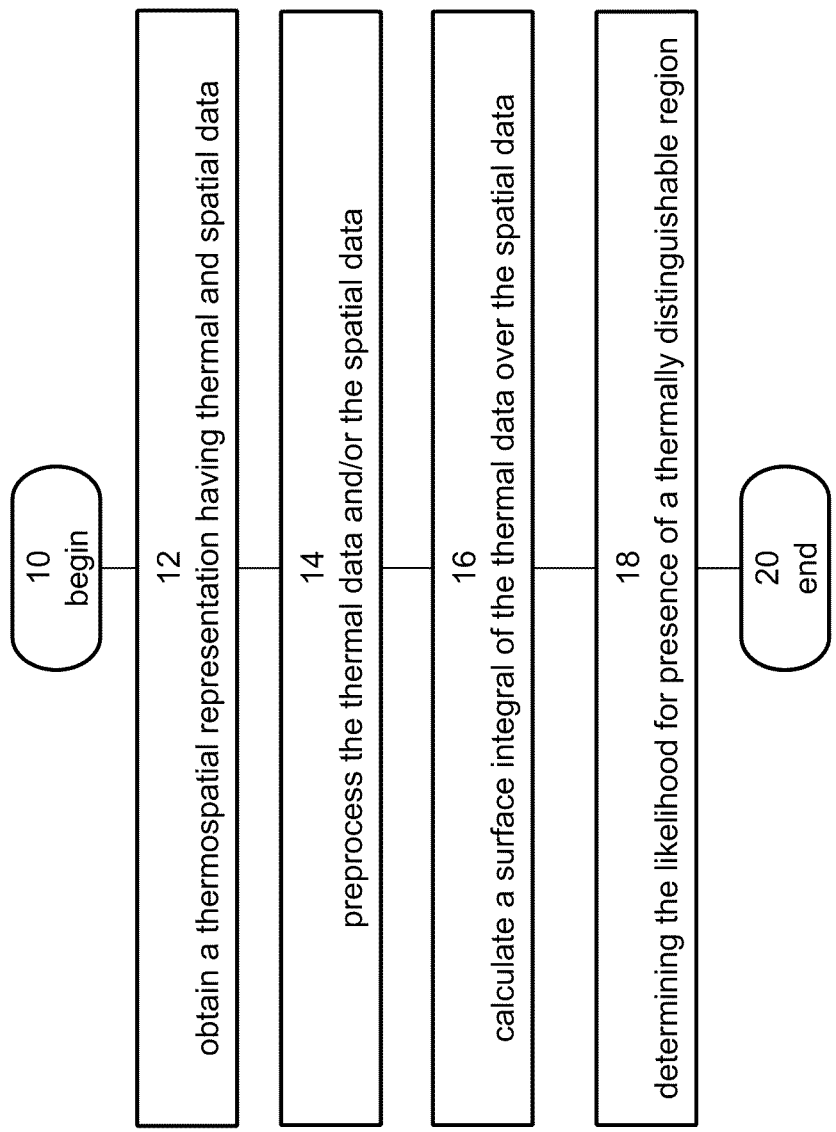
FIG. 2 is a flow chart diagram of a method suitable for analyzing a thermal image of a body section, according to some embodiments of the present invention.

FIG. 2 is a flow chart diagram of a method suitable for analyzing a thermal image of a body section, according to some embodiments of the present invention. It is to be understood that several method steps appearing in the following description or in the flowchart diagram of FIG. 2 are optional and may not be executed.

The method begins at step 10 and continues to step 12 in which a thermospatial representation of the body section is obtained. The thermospatial representation, as stated, includes thermal data representing the thermal image and spatial data representing a non-planar surface of the body section, where the thermal data is associated with spatial data. The thermospatial representation can be generated by the method or it can be generated by another method or system from which the thermospatial representation can be read by the method.

Optionally, the method continues to step 14 in which the data in the thermospatial representation is preprocessed. The preprocessing can be done for the thermal data, the spatial data, or the both spatial and thermal data.

Preprocessing of thermal data can include, without limitation, powering (e.g., squaring), normalizing, enhancing, smoothing and the like. Preprocessing of spatial data can include, without limitation, removal, replacement and interpolation of picture-elements, using various processing operations such as, but not limited to, morphological operations (e.g., erosion, dilation, opening, closing), resizing operations (expanding, shrinking), padding operations, equalization operations (e.g., via cumulative density equalization, histogram equalization) and edge detection (e.g., gradient edge detection). Representative examples of preprocessing operations are provided hereinunder.

The method proceeds to step 16 in which a surface integral of the thermal data over the surface is calculated. Formally, a surface integral of a function F over a surface S is defined a the quantity $$\int_S F dS,$$

where dS is a surface area element over S. The function F can represent a thermal related quantity, including, without limitation, temperature, thermal power density and the like. The function F can also represent intensity values or grey-levels which can be transformed via proper calibration to thermal quantities. The calculation of the surface area can be done analytically or numerically, depending on the type of information residing in the thermospatial representation.

When the spatial data in the thermospatial representation can be approximated by an analytical parameterization x and the thermal data can be associated with such parameterization via an analytical function F, the surface integral can be calculated analytically, using the expression $$\int\int_S F(\underline{x}(u,v))\left|\frac{\partial \underline{x}}{\partial u} \times \frac{\partial \underline{x}}{\partial v}\right| du dv,$$

where u and v are the variables of the parameterization x, ∂x/∂u and ∂x/∂v are partial derivatives of x(u, v) representing tangential vectors to the surface, and "×" is a cross-product. Throughout this description, vector quantities are distinguished from scalar quantities in that the vector quantities are underlined and the scalar quantities are not.

The surface integral can also be calculated without approximating an analytical parameterization for the spatial data. In this embodiment the calculation is performed numerically, using the expression $$\int_{\{S\}} F(x) \Delta S,$$

where {S} is the set of all picture-elements in the thermospatial representation (hence represents the spatial data), F(x) is the thermal quantity, grey-level or intensity associated with picture-element x∈{S}, and ΔS is the area of picture-element x. In various exemplary embodiments of the invention ΔS includes a correction factor (such as a numeric Jacobian or the like) for weighting the value of ΔS based on the shape of the surface (angle, curvature, etc.) in the neighborhood of ΔS. The surface integration $$\int_{\{S\}}$$

can be approximated as a sum $$\sum_{\{S\}}.$$

In various exemplary embodiments of the invention the surface integral is normalized by the volume of the body section. This volume can be calculated from the spatial data of the thermospatial representation.

The surface integral can also be calculated according to the expression $$\frac{1}{V}\int_S \varepsilon \sigma T^4 dS,$$

where V is the volume of the body section, T is the thermal data expressed as temperature values, ε is the emissivity of the body and σ is the Stefan-Boltzmann constant. The emissivity can be taken as fixed over the surface or it can be a function of the coordinate over the surface. When calculated according to this expression, the value of the surface integral represents thermal power density (thermal power per unit volume). The thermal power density correlates to the heat efflux from the body section and can also encompasses effects of several biological processes within the body section, including blood flow rate, metabolism and heat convection from the main body into the body section (e.g., from the chest wall to the breast in the embodiment in which the body section is a breast).

An alternative expression for calculating the surface integral for the purpose of obtaining the heat efflux is $$\frac{1}{V}\left[\int_S h(T-T_0)dS + \int_S \varepsilon\sigma(T^4 - T_0^4)dS\right],$$

where h is the heat-convection coefficient of the air and $T_0$ is the ambient temperature. In this expression for the surface integral, the first term represents heat efflux from the body section via convection, and the second represents heat efflux from the body section via radiation. An equivalent expression which includes both the convection contribution and the radiation contribution in a single term is $$\frac{1}{V}\int_S h_{eff}(T-T_0)dS,$$

where $h_{eff}$ is an effective convection coefficient.

Once the surface integral is calculated, the method optionally continues to step 18 in which the likelihood that a thermally distinguishable region is present in body section is determined based on a value of the surface integral. A thermally distinguishable region is a three-dimensional region residing in the bulk or on the surface of the in the body section and can be distinguished from its surrounding tissues by its thermal properties. Broadly speaking, a thermally distinguishable region has a temperature which is higher or lower than what expected based on its spatial location. For example, the thermally distinguishable region can have a temperature which is higher or lower than the temperature of its immediate surroundings. Yet, this need not necessarily be the case since in some situations a region can be thermally distinguishable even when its temperature is the same as the temperature of its surrounding tissue. Consider, for example, a particular region which is expected to have a temperature that is different than the temperature of its surrounding tissue. A representative example of such region is a nipple of a breast which in normal subjects has a lower temperature than its immediate surroundings. When such particular region has a temperature which is the same as its surrounding tissue, it is declared a thermally distinguishable region, because its temperature differs from its expected temperature.

In some embodiment of the present invention, the thermally distinguishable region has a temperature which differs that the temperature of a similar region in another body section. For example, when the body section is the breast of a woman, a thermally distinguishable region in one breast can have a temperature which differs from a similar region in another breast.

Presence of a thermally distinguishable region can indicate, for example, the presence of an inflammation, a benign tumor or a malignant tumor at the location of the thermally distinguishable region.

The method ends at step 20.

There is more than one way to determine the likelihood for the presence of a thermally distinguishable region is the body section. Some embodiments for the execution of step 18 are illustrated in FIGS. 3a-c.

In some embodiments, the surface integral value is compared to a value of one or more reference surface integrals, and the comparison is used for determining the likelihood for the presence of a thermally distinguishable region. Typically, but not obligatorily, the reference surface integral represents a situation in which no thermally distinguishable region is present. This embodiment is illustrated in FIG. 3a.

Figure 3A:
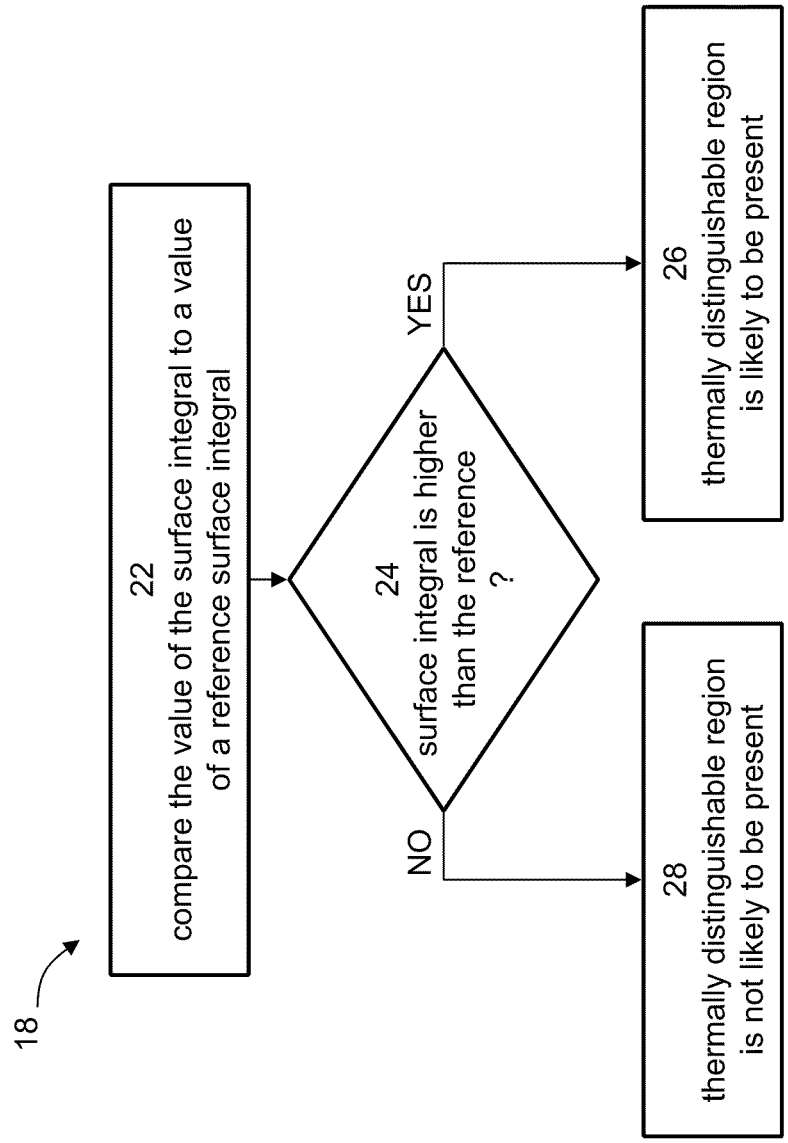
Figure 3B:
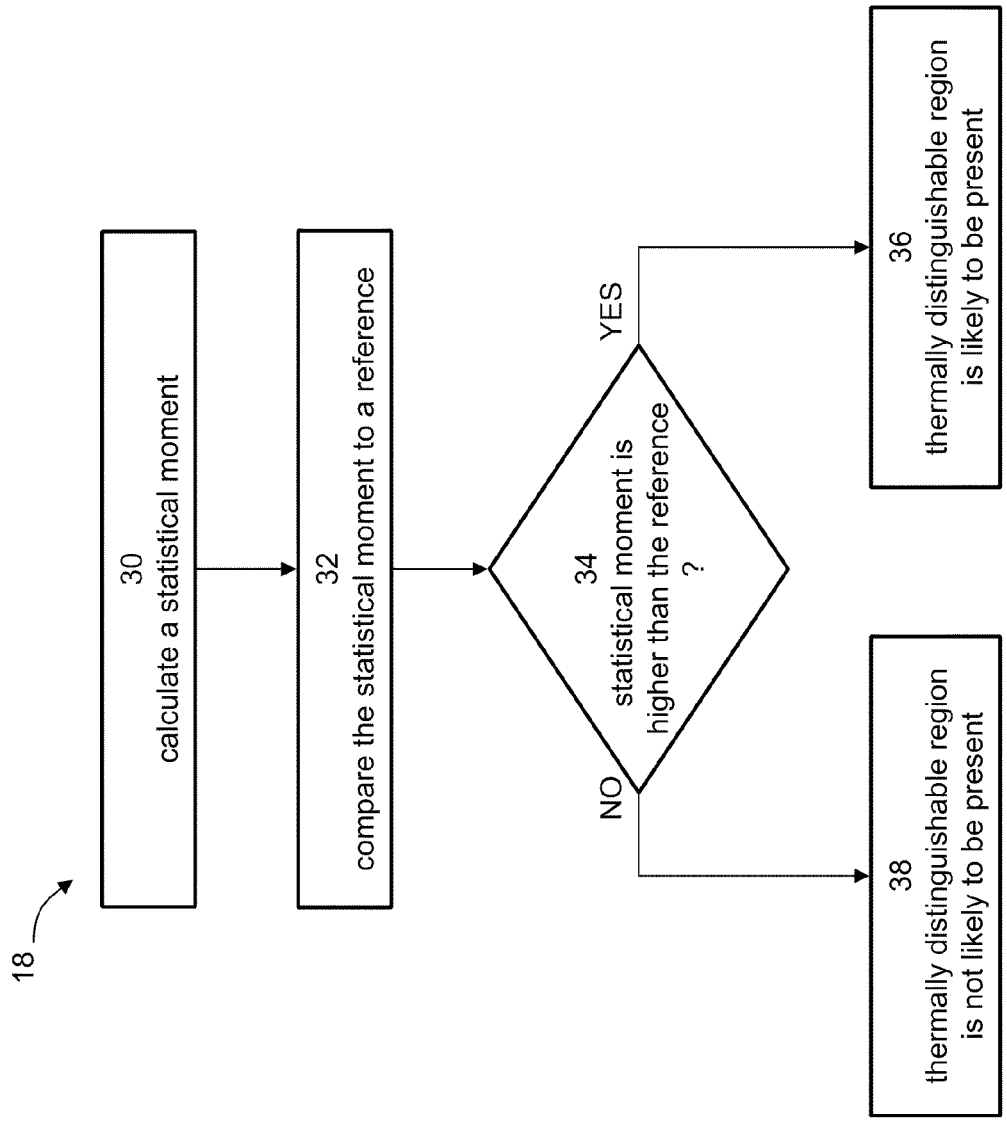

As shown in FIG. 3a, step 18 includes step 22 in which the value of the surface integral is compared to a value of one or more reference surface integrals. From step 22 the method continues to decision step 24 in which the method determines whether or not the surface integral value is higher than the value of the reference surface integral. If yes, the method continues to step 26 in which the method determines that it is likely that a thermally distinguishable region is present in the body section. If the surface integral value is not higher than the value of the reference surface integral, the method continues to step 28 in which the method determines that it is not likely that a thermally distinguishable region is present. The likelihood can also be quantified (e.g., expressed as percentage) based on the difference or ratio between the calculated surface integral and the reference surface integral.

The reference surface integral generally corresponds to a reference thermospatial representation, which can be obtained from a library or can be constructed by the method of the present embodiments.

The reference thermospatial representation can describe a reference body section other than the body section being analyzed. For example, the reference body section can be a body section which is similar in shape to the body section being analyzed. Preferably, but not obligatorily, the reference body section is devoid of thermally distinguishable region. When the body section is a breast of a woman, the reference body section can be the other breast of the same woman.

In some embodiments of the present invention the reference thermo spatial representation includes history data of the body section. For example, if the history data of a particular subject does not show presence of thermally distinguishable region in his or her body section, the data can be used as a reference. The inclusion of history data in the thermospatial representation can be achieved by recording the reference thermospatial representation and/or the calculated surface integral at a date earlier than the date at which the method is executed. This embodiment can also be useful for monitoring progress of a disease over time. Thus, for example, if the value of the surface integral is higher than its value at an earlier date, the method can determine that the thermally distinguishable region has grown. This embodiment can also be useful for monitoring efficacy of treatment. For example, when a subject having a malignant tumor is treated with chemotherapy, the value of the surface integral at different times can be calculated so as to asses the efficacy of treatment. Specifically a reduction of tumor size can result in lower value of the surface integral.

In some embodiments of the present invention the reference thermo spatial representation is obtained by means of biomedical engineering. For example, a geometry of the body section can be designed using a computer program and computer simulations can be executed (e.g., using a finite element technique or the like) to determine a threshold surface integral to be used as a reference.

FIG. 3b illustrates another embodiment for executing method step 18. In this embodiment, step 18 includes step 30 in which the value of the surface integral is used for calculating a statistical moment, such as, but not limited to, a standard deviation over the surface. From step 30 the method continues to step 32 in which the statistical moment is compared to a reference statistical moment. The reference statistical moment can be calculated using one or more reference surface integrals corresponding to a reference thermospatial representation as further detailed hereinabove.

From step 32 the method continues to decision step 34 in which the method determines whether or not the statistical moment is higher than the reference statistical moment. If yes, the method continues to step 36 in which the method determines that it is likely that a thermally distinguishable region is present in the body section. If the statistical moment is not higher than the reference statistical moment, the method continues to step 38 in which the method determines that it is not likely that a thermally distinguishable region is present. The likelihood can also be quantified (e.g., expressed as percentage) based on the difference or ratio between the statistical moment and the reference statistical moment.

FIG. 3c illustrates another embodiment for executing method step 18. In this embodiment, step 18 includes step 40 in which the value of the surface integral is used for calculating an amount or rate of heat efflux from the body section as described above. From step 40 the method continues to step 42 in which the amount or rate of heat efflux is compared to a reference. The reference can be a reference heat efflux calculated using one or more reference surface integrals corresponding to a reference thermospatial representation as further detailed hereinabove. For example, when the body section is the breast of a woman, the reference can be the heat flux calculated from a thermospatial representation of the other breast. When the body is in a steady thermal state, the convective and metabolic heats of the healthy tissues in both breasts can be estimated to be approximately the same, and a comparison between the calculated heat efflux of one breast and the heat efflux from of the other breast can be used for determining the likelihood that a tumor or inflammation exists in one of the breasts. Specifically, the breast evacuating a significantly higher amount or rate of heat is likely to have a tumor therein.

The reference can also be a threshold value taken from other studies. For example, heat production rate in healthy breast tissue is about 450 W/m$^3$ compared to about 29,000 W/m$^3$ in cancerous tissue, and blood flow rate in healthy breast tissue is about 0.00018 ml/s/ml compared to about 0.009 ml/s/ml. Thus, the existence of a cancerous tissue results in elevated heat production and elevated heat convection by blood flow. A typical ratio for characterizing the change in heat production of a cancerous region within a breast compared to a healthy breast is given by $CV/C_0V_0$, where C is the rate of heat change in the cancerous region, $C_0$ is the rate of heat change in the healthy breast tissue, V is the volume of the cancerous region and V is the volume of the breast. For a 1 cm$^3$ malignant tumor residing in a 0.5 liter breast, this ratio is about 10% when considering heat production and about 13% when considering heat convection by blood flow.

As used herein the term "about" refers to ±10%.

Such differences between cancerous and healthy tissue results in a detectable change in heat efflux from a breast having a cancerous tissue compared to a healthy breast. Thus, according to the present embodiment of the invention, the reference heat flux is a predetermined threshold selected to reflect the difference between typical healthy tissue and typical cancerous tissue. Representative example of such predetermined threshold is 1000 W/m$^3$ or more.

From step 42 the method continues to decision step 44 in which the method determines whether or not the heat flux is higher than the reference heat flux. If yes, the method continues to step 46 in which the method determines that it is likely that a thermally distinguishable region is present in the body section. If the heat flux is not higher than the reference, the method continues to step 48 in which the method determines that it is not likely that a thermally distinguishable region is present. The likelihood can also be quantified (e.g., expressed as percentage) based on the difference or ratio between the heat flux and the reference heat flux.

As delineated above, the calculation of surface integral can be preceded by preprocessing operation.

In some embodiments of the present invention, the preprocessing operation includes a definition of a region-of-interest within the surface of the body section. In these embodiments, the surface integral can be calculated over the region-of-interest. More than one region-of-interests can be defined, in which case the surface integral is preferably calculated separately for each region-of-interest. A region-of-interest can be defined, for example, as a part of the surface which is associated with high temperatures. A representative example of such region-of-interest is a region surrounding a thermally distinguishable spot on the surface. FIG. 1c schematically illustrates a thermally distinguishable spot 201. The grey area surrounding spot 201 can be defined as a region-of-interest.

Figure 4A:
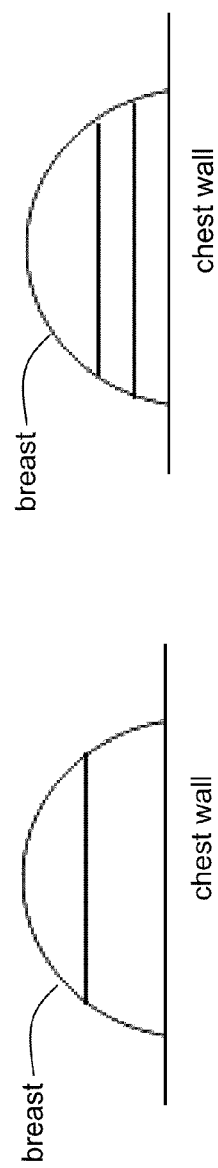
FIGS. 4A-F are schematic illustration of slicing operations, according to some embodiments of the present invention.
Figure 4B:
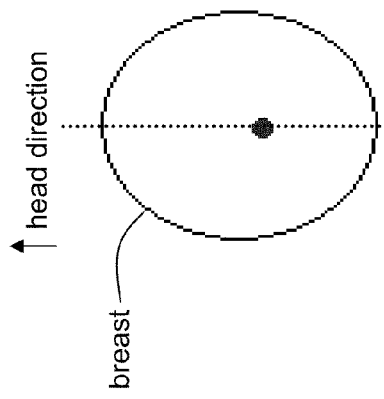
Figure 4C:
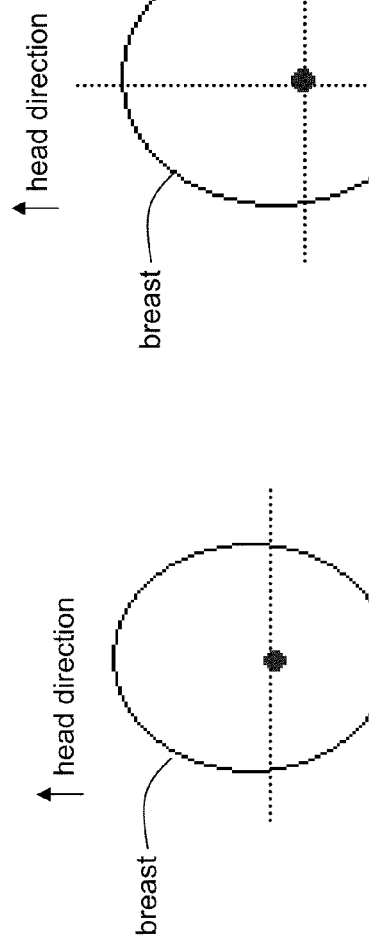
Figure 4D:
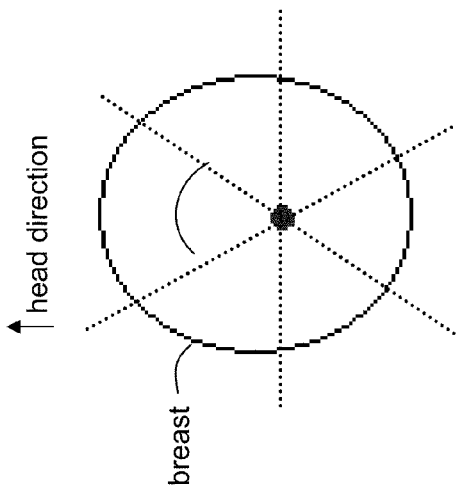
Figure 4E:
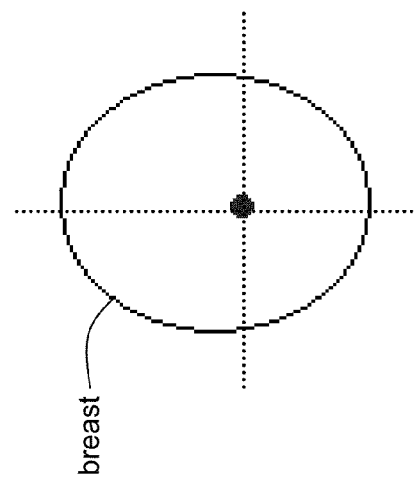
Figure 4F:
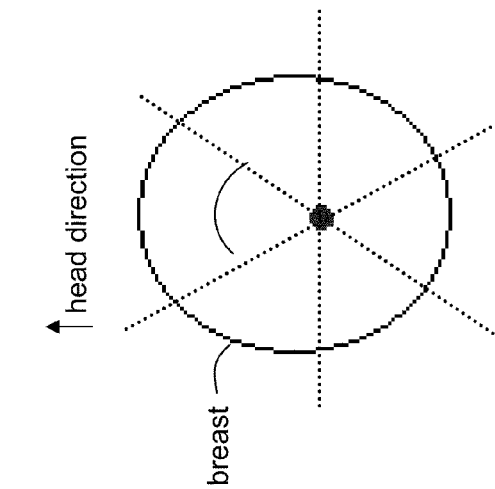

In some embodiments of the present invention the preprocessing operation includes slicing of the surface described by the spatial date to a plurality of slices. In these embodiments, the surface integral can be calculated separately for each slice. The slicing can be along a normal direction (away from the body), parallel direction, or azimuthal direction as desired. Several slicing operations are illustrated in FIGS. 4a-f, for the embodiments in which the body section is a breast. Shown in FIGS. 4a-f are two slices along a normal direction (FIG. 4a), three slices along a normal direction (FIG. 4b), two slices in a plane parallel to the body (FIGS. 4c-d), four slices in a plane parallel to the body (FIG. 4e), and six slices in a plane parallel to the body (FIG. 4f). Other slicing operations are not excluded from the scope of the present invention.

The slicing operation can be used in more than one way. In some embodiments of the present invention the slicing follower by the calculation of the surface integral is iteratively repeated and the result of each calculation is compared to other calculations. Such comparison can aid to localize the slice in which the suspected thermally distinguished region resides. In some embodiments of the present invention variation of the value of surface integral among different slices is calculated, not necessarily in iterative manner. Once the variations are calculated, they can be compared to variations one or more reference surface integral over a reference thermospatial representation, as further detailed hereinabove.

In some embodiments of the present invention the preprocessing operation includes definition of one or more spatial boundaries for the surface. For example, when the spatial data comprises data representing a surface of tissue being nearby to the body section, the method preprocessing operation can include defining a spatial boundary between the surface of the body section and surface of the nearby tissue. In this embodiment, the surface of the nearby tissue is preferably excluded from the calculation of the surface integral.

In some embodiments of the present invention the preprocessing operation includes preprocessing of the thermal data. For example, when the thermal data is provided as grey-levels or intensities, they may be converted to temperature values. Once the temperature T is known over the surface S, it can be used as the integrand of the surface integral $$\int_S F dS.$$

Optionally, a power of the temperature (e.g., $T^2$ or $T^4$) can be calculated and used as the integrand. The temperature or power thereof can also be normalized. For example, the fourth power of the temperature can be multiplied by the emissivity ε of the body and the Stefan-Boltzmann constant σ, so as to provide an integrand in units of thermal power surface densities (energy per unit time per unit area). If desired, the temperature can also be normalized by the volume of the body section or the overall area of the surface.

The temperature can also be expressed in terms of temperature difference. For example, the integrand of the surface integral can be the difference $T-T_{min}$ or some power thereof, where $T_{min}$ is the minimal temperature over the surface. Alternatively, a square averaging operation can be used, e.g., according to the expression $(T-T_{min})^2/(T_{average}-T_{min})^2$, where $T_{average}$ is the average temperature over the surface. Also contemplated are other operations, include, without limitation, logarithmic emphasis and various histogram methods.

Figure 5:
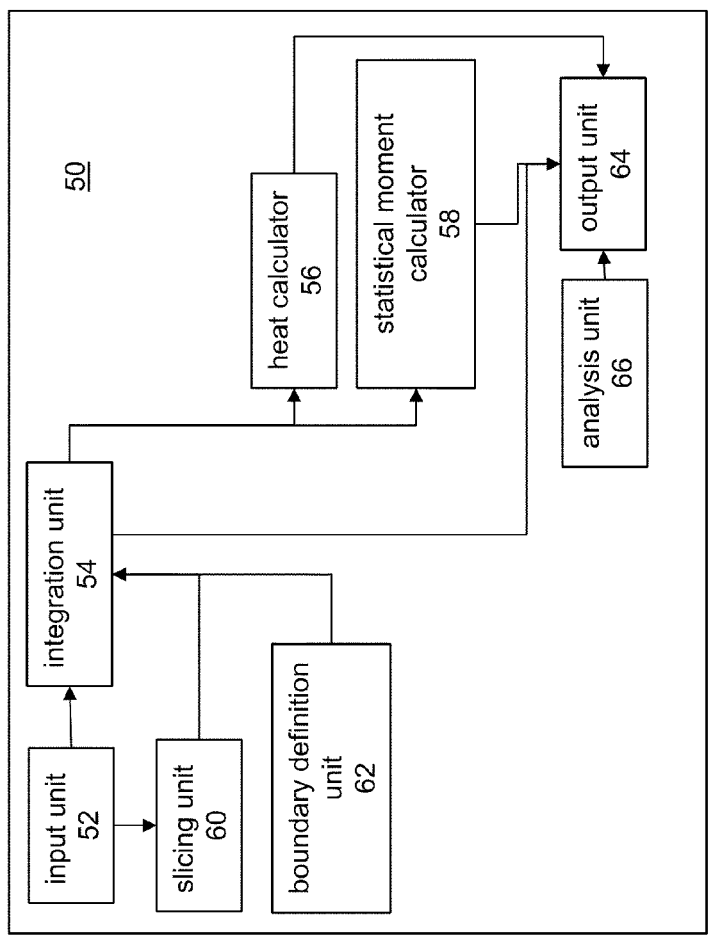
FIG. 5 is a schematic illustration of an apparatus for analyzing a thermal image of a body section, according to some embodiments of the present invention.

Reference is now made to FIG. 5 which is a schematic illustration of an apparatus 50 for analyzing a thermal image of a body section, according to some embodiments of the present invention. Apparatus 50 can be implemented in a data processor or a computer system and can be used for executing one or more of the method steps described above. Data flow channels between the various components of apparatus 50 are shown as arrows in FIG. 5.

Apparatus 50 comprises an input unit 52 for receiving the thermospatial representation and an integration unit 54 which calculates the surface integral of thermal data over the surface, as further detailed hereinabove. In some embodiments of the present invention apparatus 50 comprises a heat calculator 56 which calculates the amount or rate of heat efflux from the body section using the value of surface integral, as further detailed hereinabove. In some embodiments of the present invention apparatus 50 comprises a statistical moment calculator 58 which calculates a statistical moment of thermal data, such as a standard deviation or the like, as further detailed hereinabove.

In some embodiments of the present invention apparatus 50 comprises a slicing unit for slicing the surface to a plurality of slices. In these embodiments, integration unit 54 preferably receives the slices from slicing unit 60 and calculates the surface integral separately for each slice, as further detailed hereinabove.

In some embodiments of the present invention apparatus 50 comprises a boundary definition unit 62 which defines the spatial boundary between the surface of the body section and the surface of nearby tissue. In these embodiments, integration unit 54 preferably receives the slices from unit 62 and excludes the surface of the nearby tissue from the calculation of the surface integral.

Apparatus 50 preferably comprises an output unit 64 which issues a report regarding the value of surface integral. Optionally and preferably, apparatus 50 comprises an analysis unit 66 which analyzes the results obtained from the various components (integration unit 54, heat calculator 56 and/or statistical moment calculator 58). For clarity of presentation, data flow to analysis unit 66 is not shown. Analysis unit 66 provides the result of the analysis to output unit 64, which includes the results of the analysis in the report. The analysis performed by unit 66 can include the determination of the likelihood that a thermally distinguishable region is present in the body section, as further detailed hereinabove.

Figure 6:
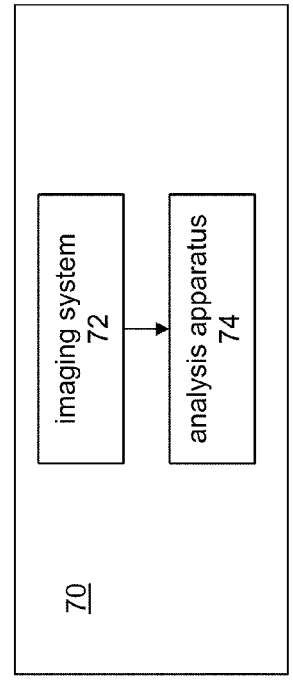
FIG. 6 is a schematic illustration of an imaging and processing system, according to some embodiments of the present invention.

Reference is now made to FIG. 6 which is a schematic illustration of an imaging and processing system 70, according to some embodiments of the present invention. System 70 comprises a thermospatial imaging system 72 which provides a thermospatial representation of a body section, and an analysis apparatus 74 for analyzing the thermospatial representation. The principles and operations of analysis apparatus 74 are similar to the principles and operations of apparatus 50 described above. In some embodiments of the present invention apparatus 74 is apparatus 50.

The following description is of techniques for obtaining the thermo spatial representation, according to various exemplary embodiments of the present invention. The techniques described below can be employed by any of the method and apparatus described above.

A thermospatial representation or image can be generated obtained by acquiring one or more thermographic images and mapping the thermographic image(s) on a 3D spatial representation.

Figure 7A:
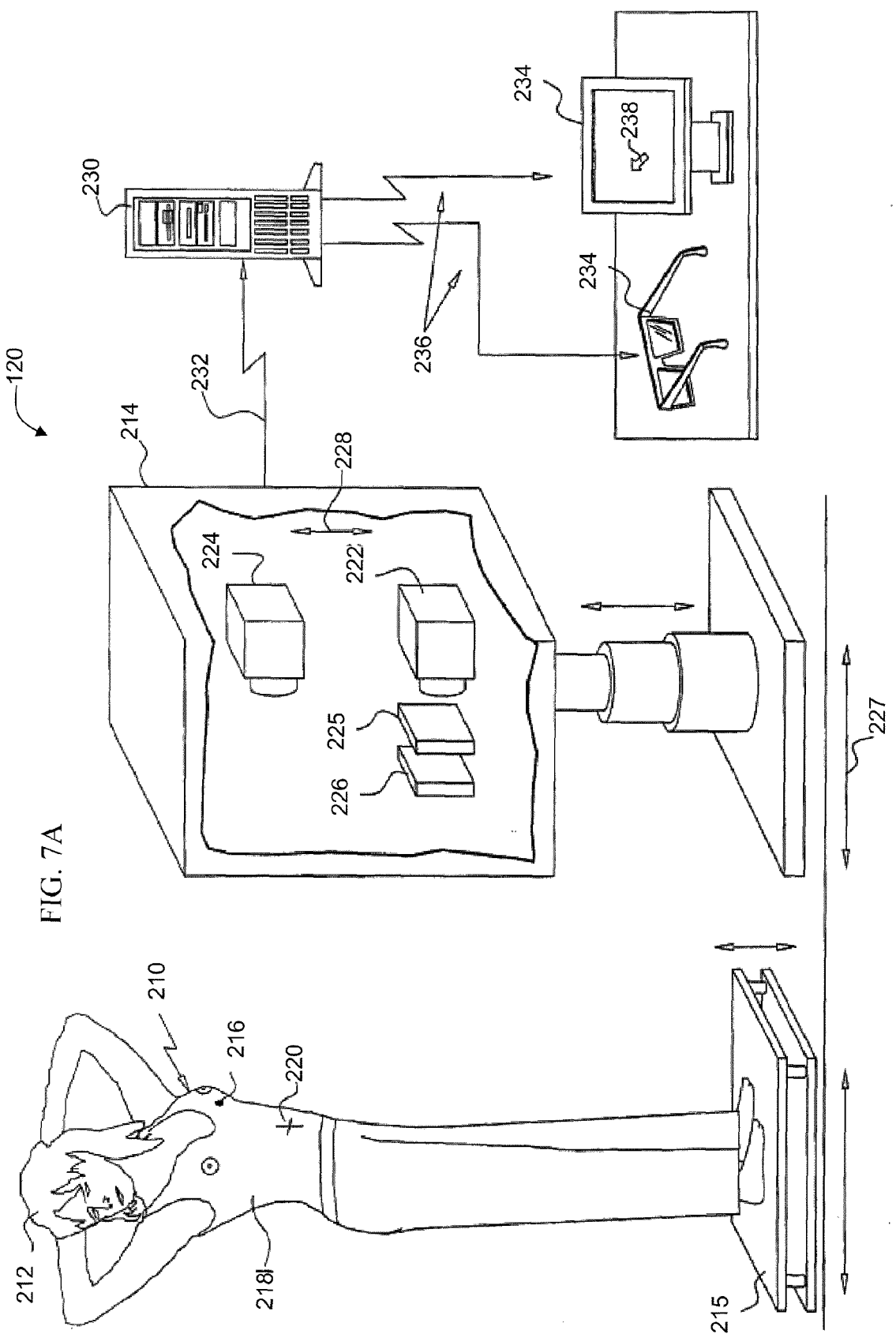
FIGS. 7A-F and 8A-E are schematic illustration of a thermospatial imaging system, according to various exemplary embodiments of the present invention.

Reference is now made to FIG. 7a which is a schematic illustration of a thermospatial imaging system 120 in accordance with preferred embodiments of the present invention. As shown in FIG. 7a, a living body 210 or a part thereof of a person 212 is located in front of an imaging device 214. The person 212, may be standing, sitting or in any other suitable position relative to imaging device 214. Person 212 may initially be positioned or later be repositioned relative to imaging de by positioning device 215, which typically comprises a platform moving on a rail, by force of an engine, or by any other suitable force. Additionally, a thermally distinguishable object 216, such as a tumor, may exist in body 210 of person 212. For example, when body 210 comprises a breast, object 216 can be a breast tumor such as a cancerous tumor.

In accordance with a preferred embodiment of the present invention, person 212 may be wearing a clothing garment 218, such as a shirt. Preferably, clothing garment 218 may be non-penetrable or partially penetrable to visible wavelengths such as 400-700 nanometers, and may be penetrable to wavelengths that are longer than visible wavelengths, such as infrared wavelengths. Additionally, a reference mark 220 may be located close to person 212, preferably directly on the body of person 212 and in close proximity to body 210. Optionally and preferably, reference mark 220 is directly attached to body 210. Reference mark 220 may typically comprise a piece of material, a mark drawn on person 212 or any other suitable mark, as described herein below.

Imaging device 214 typically comprises at least one visible light imaging device 222 that can sense at least visible wavelengths and at least one thermographic imaging de which is sensitive to infrared wavelengths, typically in the range of as 3-5 micrometer and/or 8-12 micrometer. Typically imaging devices 222 and 224 are capable of sensing reference mark 220 described hereinabove.

Optionally, a polarizer 225 may be placed in front of visible light imaging device 222. As a further alternative, a color filter 226, which may block at least a portion of the visible wavelengths, may be placed in front of visible light imaging device 222.

Typically, at least one visible light imaging device 222 may comprise a black-and-white or color stills imaging device, or a digital imaging device such as CCD or CMOS. Additionally, at least one visible light imaging device 222 may comprise a plurality of imaging elements, each of which may be a three-dimensional imaging element.

Optionally and preferably, imaging device 214 may be repositioned relative to person 212 by positioning device 227. As a further alternative, each of imaging devices 222 and 224 may also be repositioned relative to person 212 by at least one positioning device 228. Positioning device 227 may comprise an engine, a lever or any other suitable force, and may also comprise a rail for moving imaging device 214 thereon. Preferably, repositioning device 228 may be similarly structured.

Data acquired by visible light imaging device 222 and thermographic imaging de is output to a data processor 230 via a communications network 232, and is typically analyzed and processed by an algorithm running on the data processor. The resulting data may be displayed on at least one display device 234, which is preferably connected to data processor 230 via a communications network 236. Data processor 230 typically comprises a PC, a PDA or any other suitable data processor. Communications networks 232 and 236 typically comprise a physical communications network such as an internet or intranet, or may alternatively comprise a wireless network such as a cellular network, infrared communication network, a radio frequency (RF) communications network, a blue-tooth (BT) communications network or any other suitable communications network.

In accordance with a preferred embodiment of the present invention dis typically comprises a screen, such as an LCD screen, a CRT screen or a plasma screen. As a further alternative dis may comprise at least one visualizing device comprising two LCDs or two CRTs, located in front of a user's eyes and packaged in a structure similar to that of eye-glasses. Preferably, dis also displays a pointer 238, which is typically movable along the X, Y and Z axes of the displayed model and may be used to point to different locations or elements in the displayed data.

Reference is now made to FIGS. 7b-f and 8a-e which illustrate the various operation principles of thermospatial imaging system 120, in accordance with various exemplary embodiments of the invention.

The visible light imaging is described first, with reference to FIGS. 7b-f, and the thermographic imaging is described hereinafter, with reference to FIGS. 8a-e. It will be appreciated that the visible light image data acquisition described in FIGS. 7b-f may be performed before, after or concurrently with the thermographic image data acquisition described in FIGS. 8a-e.

Referring to FIGS. 7b-f, person 212 comprising body 210 is located on positioning device 214 in front of imaging device 214, in a first position 240 relative to the imaging device. First image data of body 210 is acquired by visible light imaging device 22, optionally through polarizer 225 or as an alternative option through color filter 226. The advantage of using a color filter is that it can improve the signal-to-noise ratio, for example, when the person is illuminated with a pattern or mark of specific color, the color filter can be used to transmit only the specific color thereby reducing background readings. Additionally, at least second image data of body 210 is acquired by visible light imaging device 222, such that body 210 is positioned in at least a second position 242 relative to imaging device 214. Thus, the first, second and optionally more image data are acquired from at least two different viewpoint of the imaging device relative to body 210.

Figure 7B:
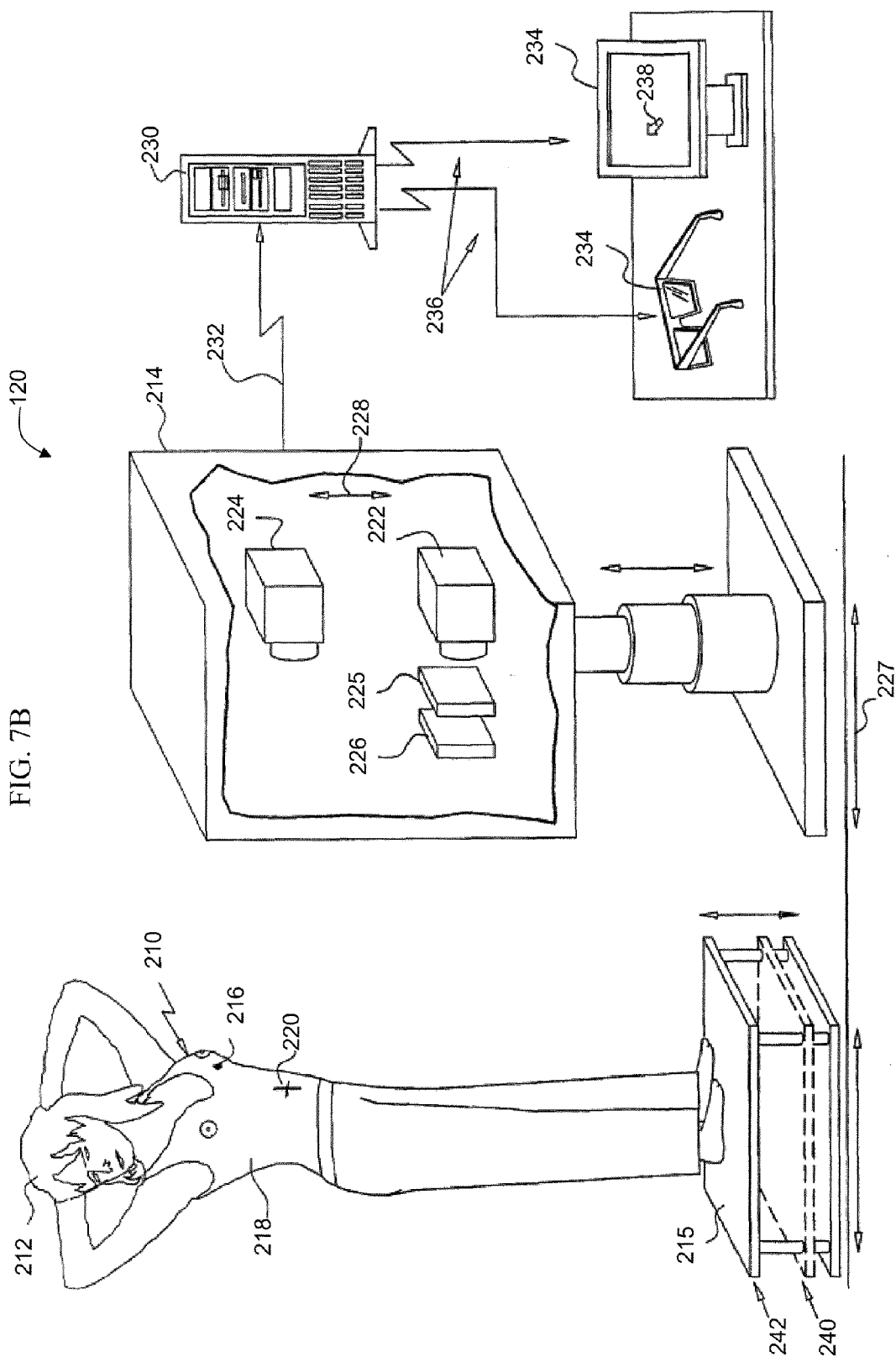
Figure 7C:
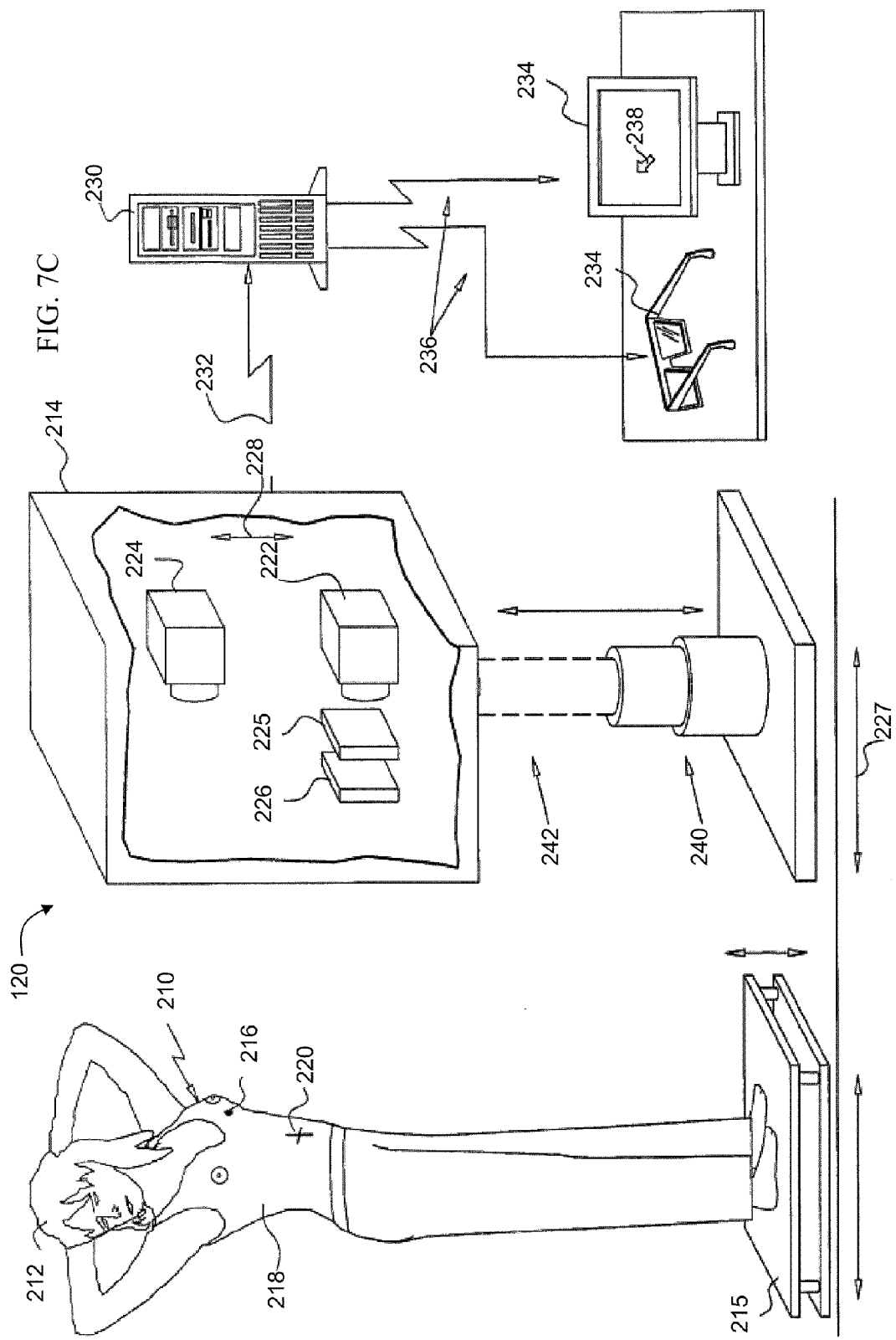
Figure 7D:
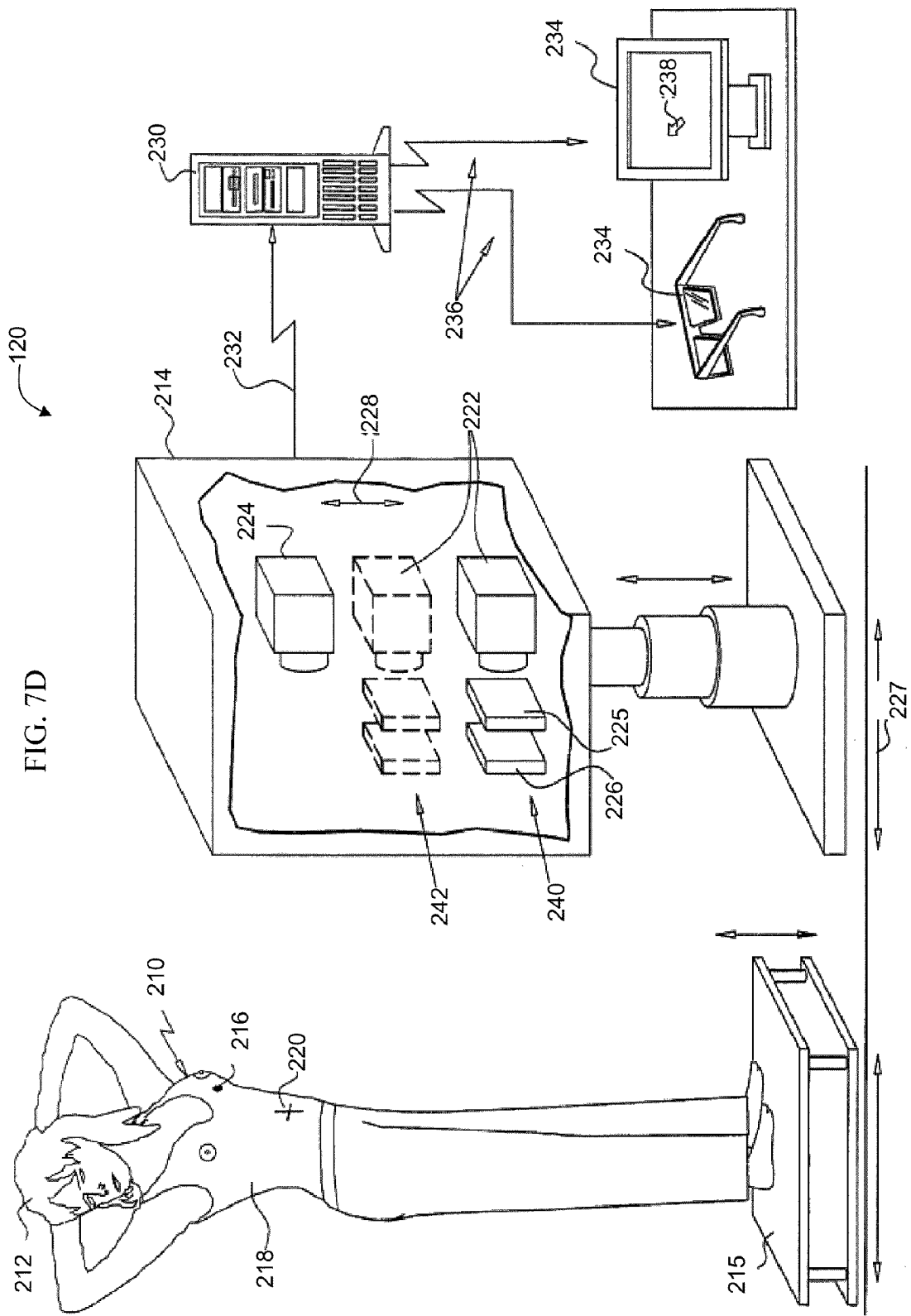
Figure 7E:
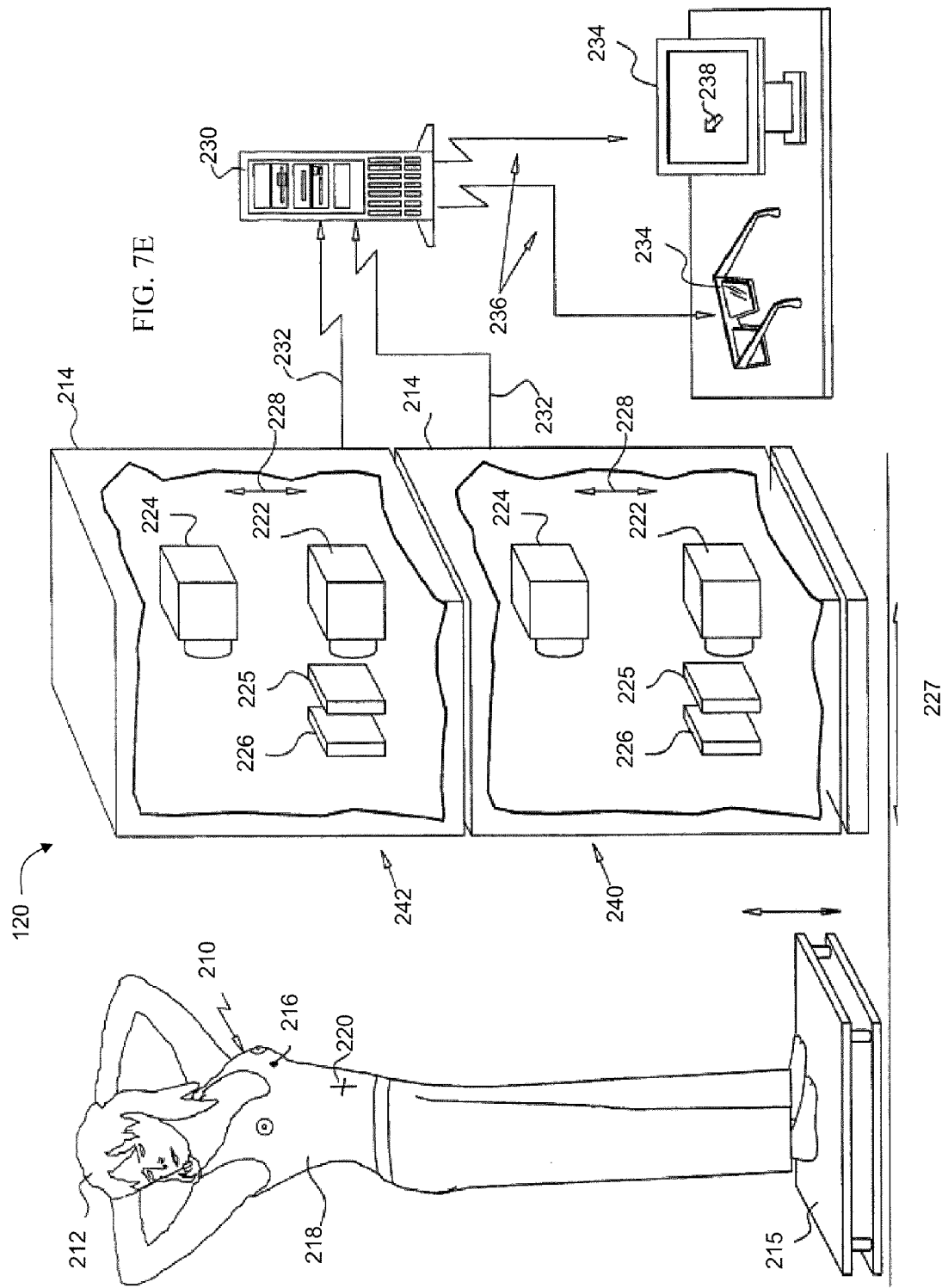
Figure 7F:
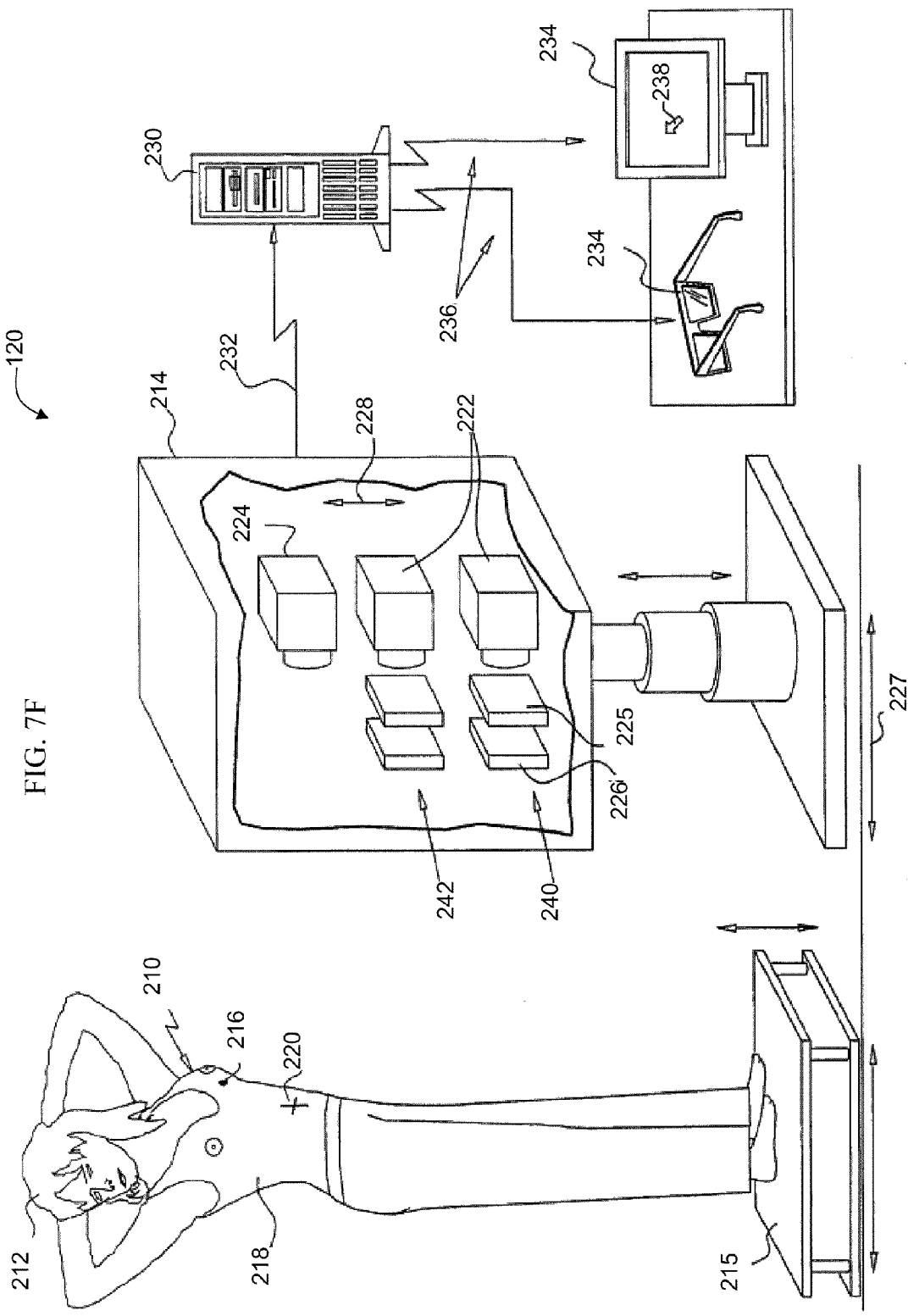

The second relative position 242 may be configured by repositioning person 212 using positioning device 215 as seen in FIG. 7b, by repositioning imaging device 214 using positioning device 227 as seen in FIG. 7c or by repositioning imaging device 222 using positioning device 228 as seen in FIG. 7d. As a further alternative, second relative position 242 may be configured by using two separate imaging devices 214 as seen in FIG. 7e or two separate visible light imaging device 210 as seen in FIG. 7f.

Referring to FIGS. 8a-e, person 212 comprising body 210 is located on positioning device 215 in front of imaging device 214, in a first position 244 relative to the imaging device. First thermographic image data of body 210 is acquired by thermographic imaging device 224. Optionally and preferably at least second thermographic image data of body 210 is acquired by thermographic imaging device 224, such that body 210 is positioned in at least a second position 242 relative to imaging device 214. Thus, the first, second and optionally more thermographic image data are acquired from at least two different viewpoints of the thermographic imaging device relative to body 210.

Figure 8A:
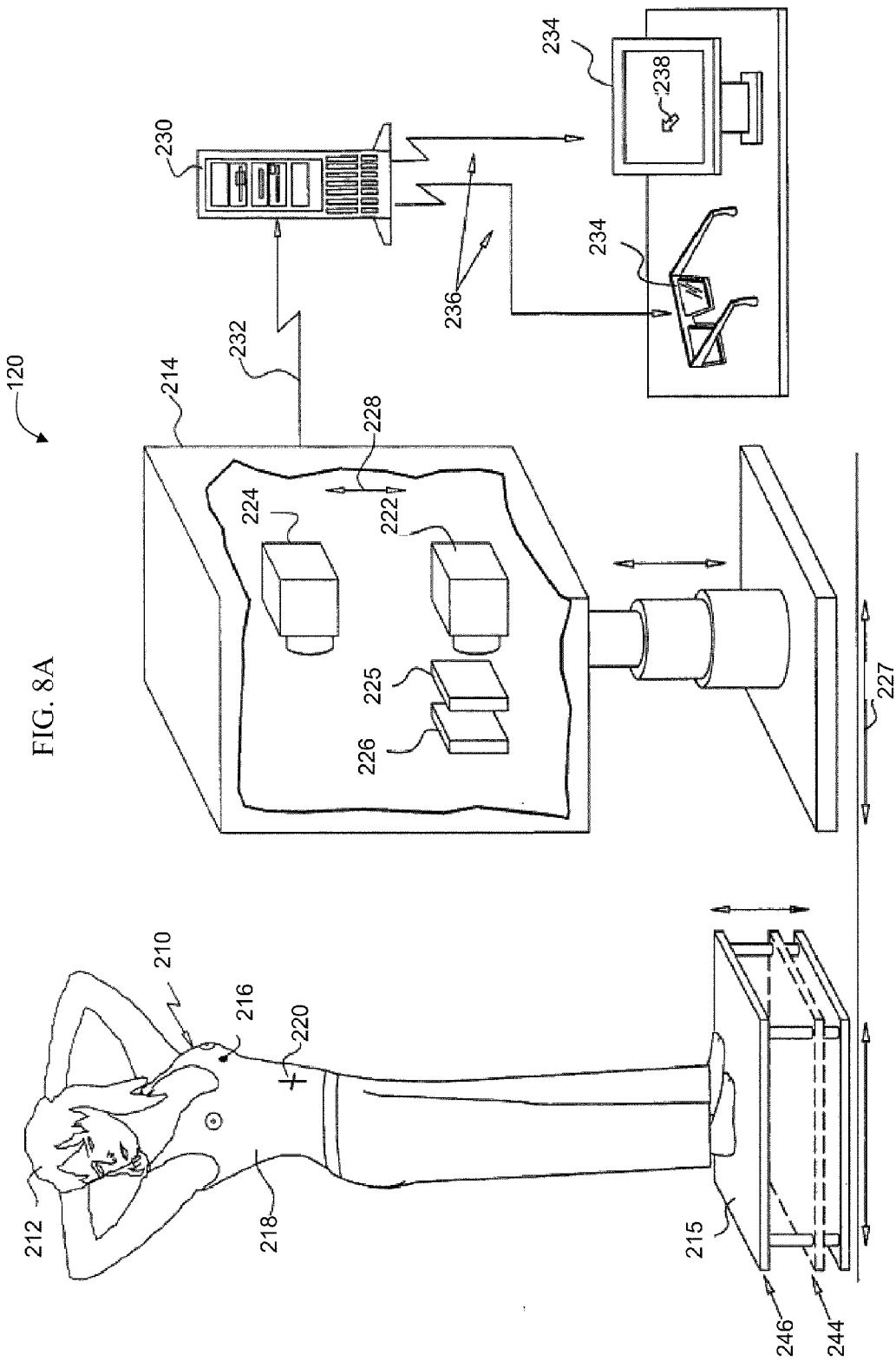
Figure 8B:
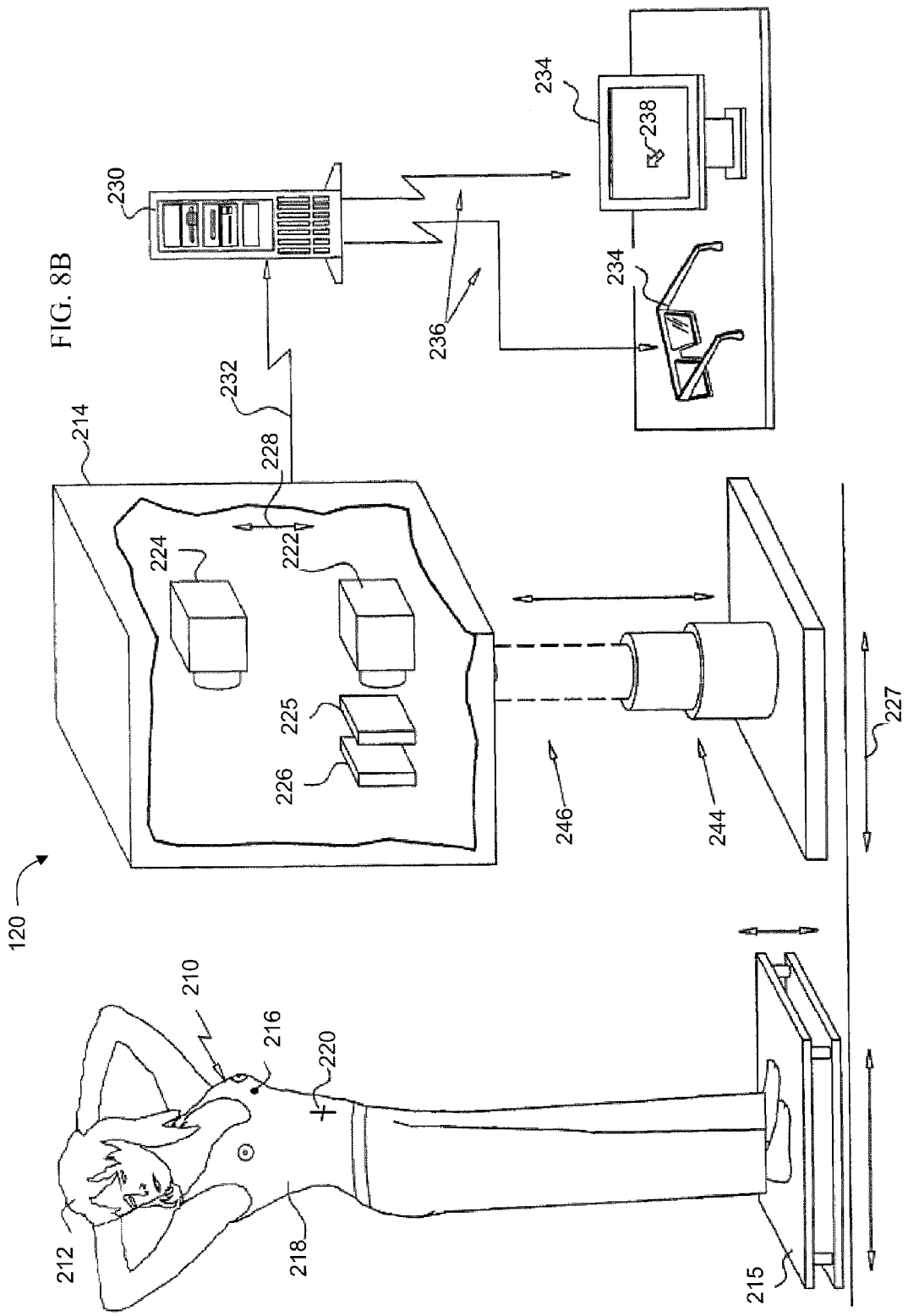
Figure 8C:
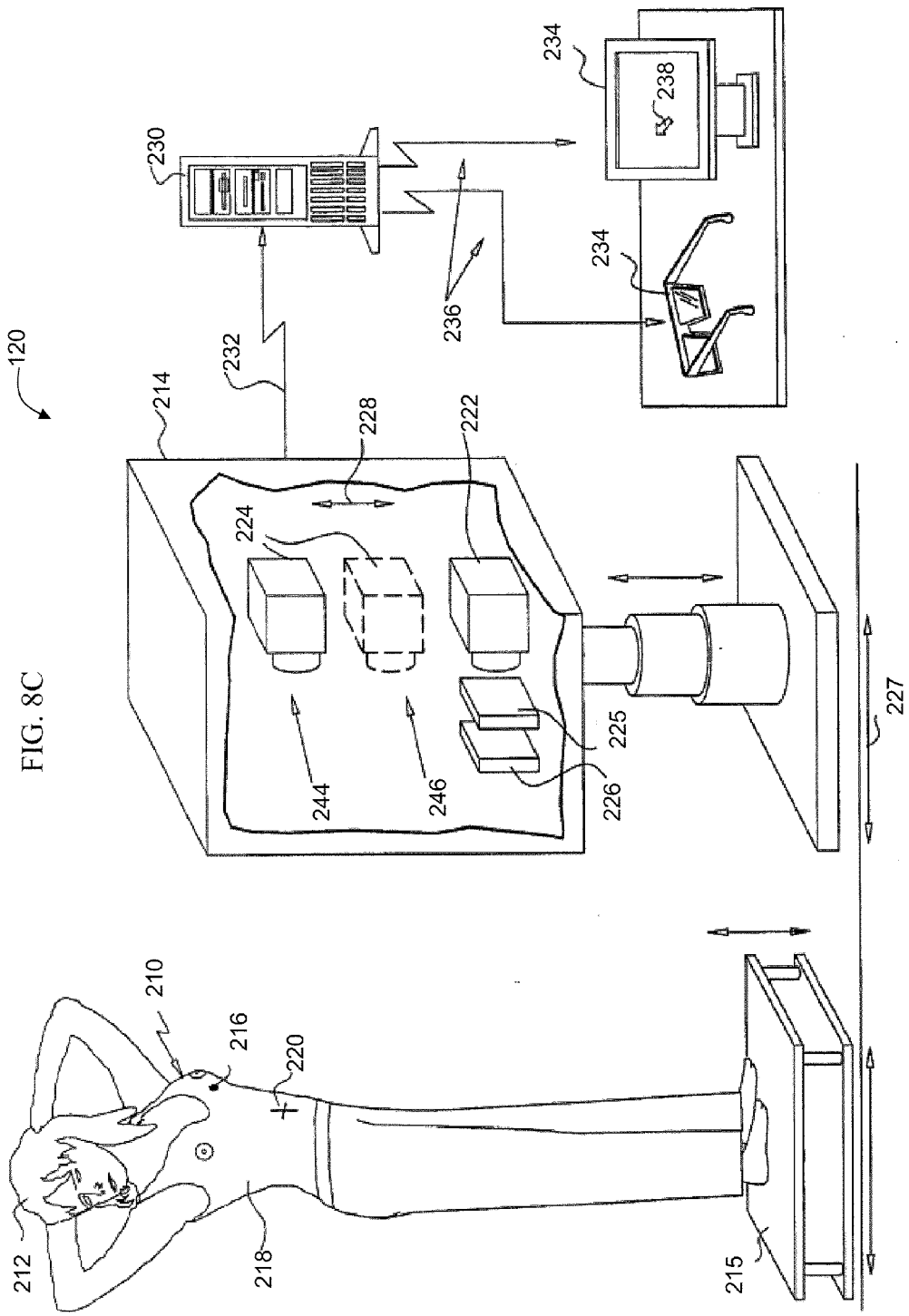
Figure 8D:
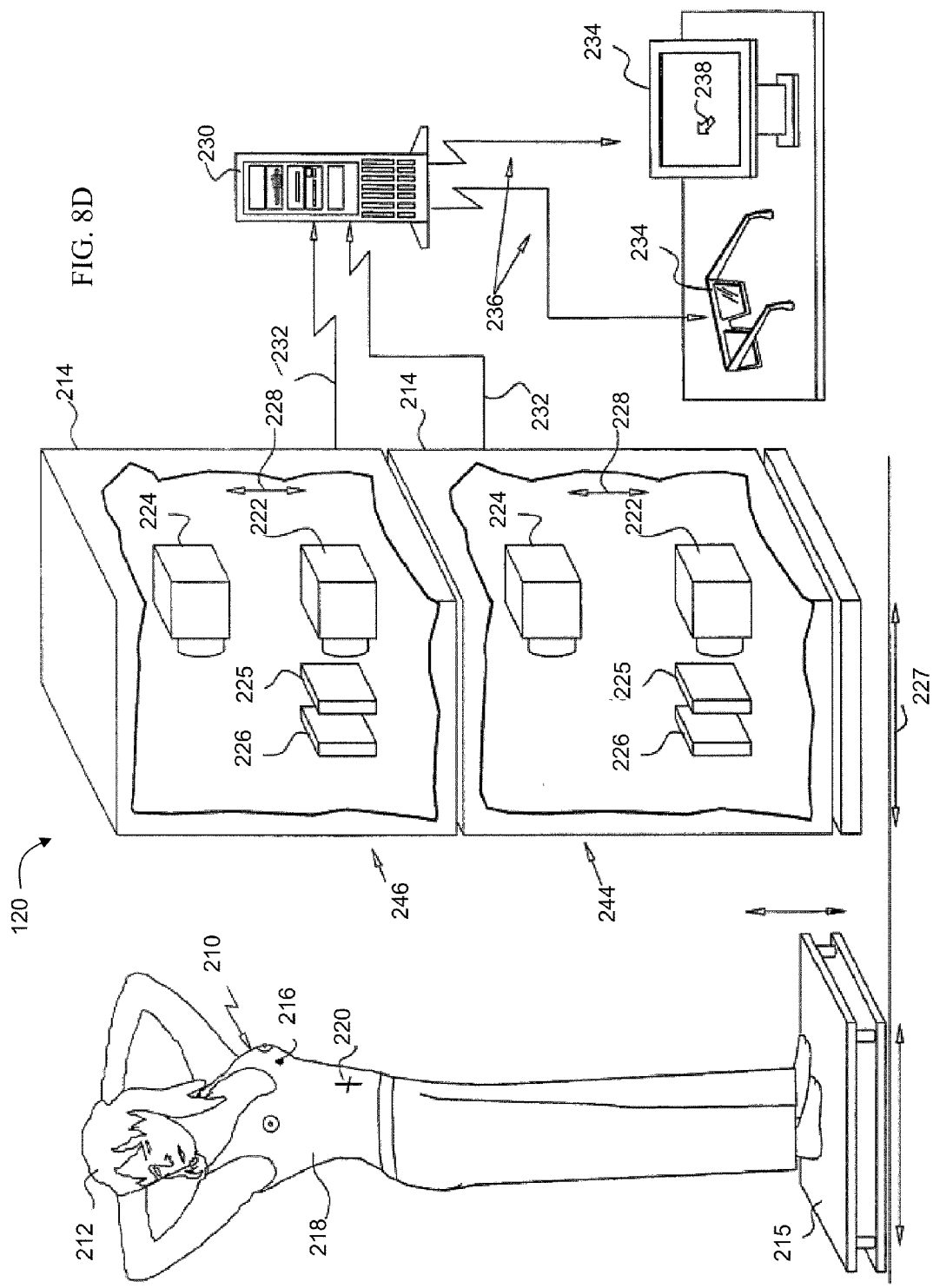
Figure 8E:
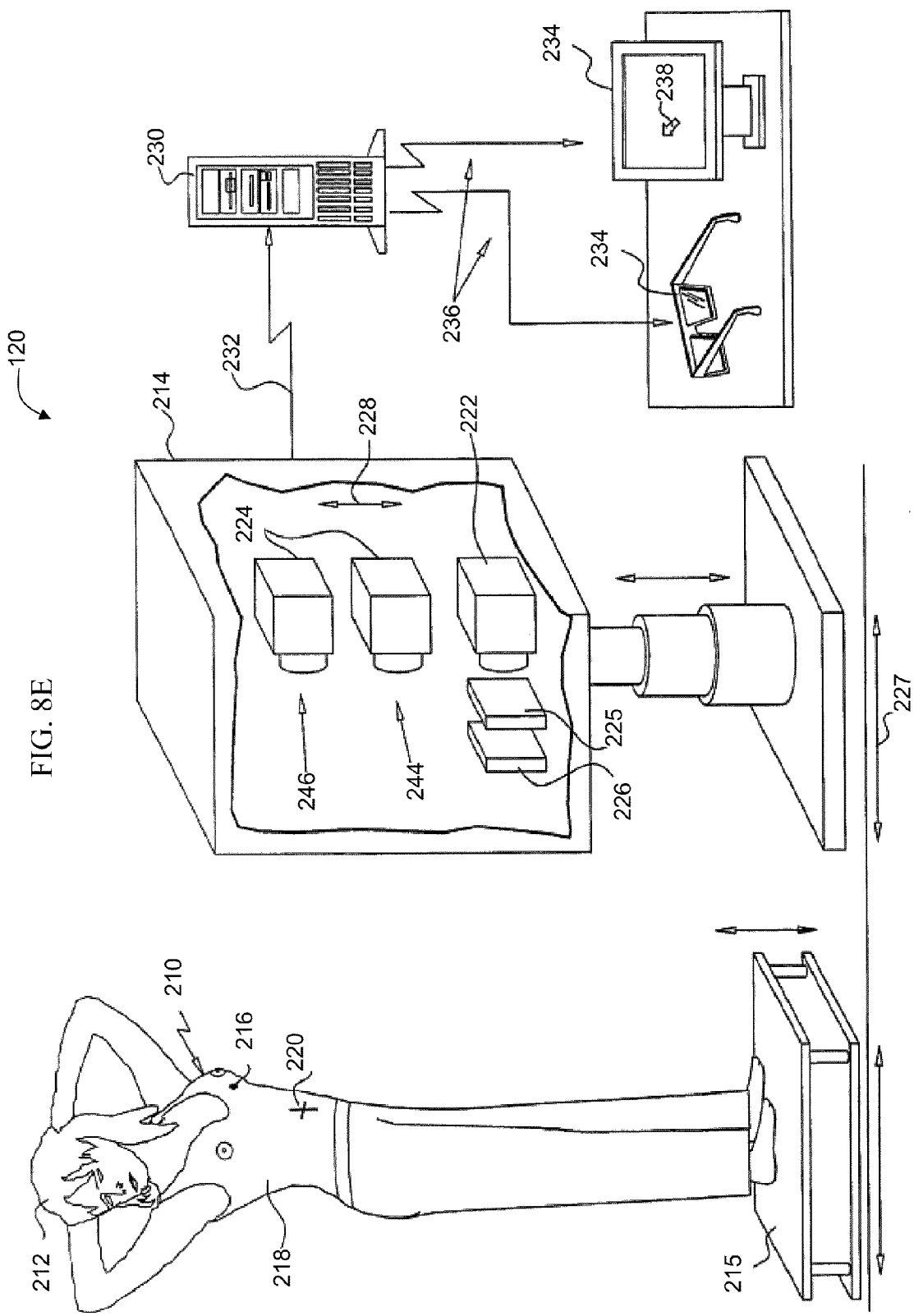

The second relative position 246 may be configured by repositioning person 212 using positioning device 215 as seen in FIG. 8a, by repositioning imaging de using positioning device 227 as seen in FIG. 8b, or by repositioning thermographic imaging device 224 using positioning device 228 as seen in FIG. 8c. As a further alternative, the second relative position 246 may be configured by using two separate imaging devices 214 as seen in FIG. 8d or two separate thermographic imaging devices 224 as seen in FIG. 8e.

Image data of body 210 may be acquired by thermographic imaging device 224, by separately imaging a plurality of narrow strips of the complete image of body 210. Alternatively, the complete image of body 210 is acquired by the thermographic imaging device, and the image is sampled in a plurality of narrow strips or otherwise shaped portions for processing. As a further alternative, the imaging of body 210 may be performed using different exposure times.

The thermographic and visible light image data obtained from imaging device 214 is preferably analyzed and processed by data processor 230 as follows. Image data acquired from imaging device 222 is processed by data processor 230 to build a three-dimensional spatial representation of body 210, using algorithms and methods that are well known in the art, such as the method described in U.S. Pat. No. 6,442,419 which is hereby incorporated by reference as if fully set forth herein. The 3D spatial representation preferably comprises the location of reference marker 220 (cf. FIG. 1a). Optionally and preferably, the 3D spatial representation comprises information relating to the color, hue and tissue texture of body 210. Thermographic image data acquired from imaging device 224 is processed by data processor 230 to build a thermographic three-dimensional model of body 210, using algorithms and methods that are well known in the art, such as the method described in U.S. Pat. No. 6,442,419. The thermographic 3D model preferably comprises reference marker 220 (cf. FIG. 1b). The thermographic 3D model is then mapped by processor 230 onto the 3D spatial representation, e.g., by aligning reference marker 220, to form the thermospatial image.

The terms "comprises", "comprising", "includes", "including", "having" and their conjugates mean "including but not limited to".

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of analyzing a thermal image of a body section, comprising:
    obtaining a 3D thermospatial representation having thermal data representing the thermal image and 3D spatial data representing a non-planar surface of the body section, said thermal data being associated with said 3D spatial data;
    calculating by a computer processor a surface integral of said thermal data over said surface using a correction factor for weighting the value of picture-elements in said thermospatial representation; and
    determining the likelihood that a thermally distinguishable region is present in said body section, based on a value of said surface integral.

2. The method of claim 1, wherein said determining said likelihood comprises comparing said surface integral value to a value of at least one reference surface integral corresponding to a reference thermospatial representation.

3. The method of claim 2, wherein said at least one reference thermospatial representation describes a reference body other than the body section and being similar in shape thereto.

4. The method of claim 3, wherein the body section is a first breast of a woman and said reference body section is a second breast of said woman.

5. The method of claim 3, wherein the body section is a part of a first breast of a woman and said reference body section is a part of a second breast of said woman.

6. The method of claim 2, wherein said at least one reference thermospatial representation comprises history data of the body section.

7. The method of claim 2, wherein said reference surface integral corresponds to a reference body section other than the body section and being devoid of thermally distinguishable region therein.

8. The method of claim 1, further comprising using said surface integral value for calculating an amount or rate of heat efflux from the body section.

9. The method of claim 8, wherein said determining said likelihood comprises comparing said amount or rate of heat efflux to an amount or rate of heat efflux calculated using a value of at least one reference surface integral corresponding to a reference thermospatial representation.

10. The method of claim 1, further comprising using said surface integral value for calculating a statistical moment of said thermal data over said surface.

11. The method of claim 10, wherein said determining said likelihood comprises comparing said statistical moment to a statistical moment calculated using a value of at least one reference surface integral corresponding to a reference thermospatial representation.

12. The method of claim 1, further comprising defining a region-of-interest within said surface wherein said surface integral is calculated over said region-of-interest.

13. The method of claim 1, further comprising slicing said surface to a plurality of slices wherein said surface integral is calculated separately for each slice.

14. The method of claim 13, further comprising iteratively repeating said slicing and said calculation of said surface integral.

15. The method of claim 13, wherein said determining said likelihood comprises calculating variation of a value of said surface integral among different slices.

16. The method of claim 15, wherein said determining said likelihood comprises comparing said variations to variations of at least one reference surface integral over a reference thermospatial representation.

17. The method of claim 1, wherein said spatial data comprises data representing a surface of tissue being nearby to the body section and the method comprises defining a spatial boundary between the surface of the body section and said surface of said nearby tissue.

18. A method of monitoring evolution of a tumor in a body section, the method comprising:
    (a) using an thermospatial imaging system for generating a series of 3D thermospatial representations, each having thermal data representing the thermal image and 3D spatial data representing a non-planar surface of the body section, said thermal data being associated with said spatial data;

(b) calculating by a computer processor, for each thermospatial representation, a surface integral of respective thermal data over respective surface using a correction factor for weighting the value of picture-elements in said thermospatial representation, thereby providing a series of surface integral values; and (c) comparing at least two of said surface integral values, and using said comparison for assessing whether the size of the tumor varies, thereby monitoring the existence and/or evolution of the tumor.

19. The method of claim 18, further comprising applying a destructive treatment to the tumor, wherein said comparison is used for assessing whether the size of the tumor is stable reduced.

20. Apparatus for analyzing a thermal image of a body section, comprising:

an input unit configured to receive a 3D thermospatial representation having thermal data representing the thermal image and 3D spatial data representing a non-planar surface of the body section, said thermal data being associated with said spatial data;

an integration unit having circuit configured to calculate a surface integral of said thermal data over said surface, using a correction factor for weighting the value of picture-elements in said thermospatial representation; and an output unit configured to issue a report regarding a value of said surface integral.

21. The apparatus of claim 20, wherein the apparatus further comprises a heat calculator for calculating an amount or rate of heat efflux from the body section using a value of said surface integral.

22. The apparatus of claim 20, wherein the apparatus further comprises a statistical moment calculator for calculating statistical moment of said thermal data over said surface using a value of said surface integral.

23. The apparatus of claim 20, wherein the apparatus further comprises a slicing unit for slicing said surface to a plurality of slices wherein said surface integral is calculated separately for each slice.

24. The apparatus of claim 20, wherein said spatial data comprises data representing a surface of tissue being nearby to the body section and the apparatus comprises a boundary definition unit for defining a spatial boundary between the surface of the body section and said surface of said nearby tissue.

25. An imaging and processing system, comprising:

a thermospatial imaging system operable to provide a 3D thermospatial representation of a body section, said thermospatial representation having thermal data representing the thermal image and 3D spatial data representing a non-planar surface of the body section, said thermal data being associated with said spatial data; and apparatus for analyzing a thermal image of a body section, said apparatus comprising:

an input unit configured to receive said thermospatial representation;

an integration unit having circuit configured to calculate a surface integral of said thermal data over said surface, using a correction factor for weighting the value of picture-elements in said thermospatial representation; and an output unit configured to issue a report regarding a value of said surface integral.

* * * * *